(12) United States Patent
Holbert, Jr. et al.

(10) Patent No.: US 12,396,900 B2
(45) Date of Patent: Aug. 26, 2025

(54) REUSABLE PAD

(71) Applicant: Standard Textile Co., Inc., Cincinnati, OH (US)

(72) Inventors: Richard Holbert, Jr., Loveland, OH (US); Warren William Gerhardt, Spartanburg, SC (US); Rajib Mondal, Cincinnati, OH (US); Ken Kaiser, Cincinnati, OH (US); Benjamin Robers, Cincinnati, OH (US); Sara Arvidson Broadaway, Woodruff, SC (US)

(73) Assignee: Standard Textile Co., Inc., Cincinnati, OH (US)

( * ) Notice: Subject to any disclaimer, the term of this patent is extended or adjusted under 35 U.S.C. 154(b) by 690 days.

(21) Appl. No.: 17/711,483

(22) Filed: Apr. 1, 2022

(65) Prior Publication Data

US 2022/0323266 A1    Oct. 13, 2022

Related U.S. Application Data

(60) Provisional application No. 63/170,618, filed on Apr. 5, 2021.

(51) Int. Cl.
*A61F 13/47* (2006.01)
*A61F 13/15* (2006.01)
*A61F 13/53* (2006.01)

(52) U.S. Cl.
CPC ........ *A61F 13/47* (2013.01); *A61F 13/15268* (2013.01); *A61F 13/53* (2013.01);
(Continued)

(58) Field of Classification Search
CPC .... A61F 13/47; A61F 13/15268; A61F 13/53; A61F 2013/15276; A61F 2013/530255;
(Continued)

(56) References Cited

U.S. PATENT DOCUMENTS 4,289,513 A * 9/1981 Brownhill .......... F02M 25/0854
428/323
RE30,972 E     6/1982 Kyle et al.
(Continued)

FOREIGN PATENT DOCUMENTS

CN      209253337 U      8/2019
EP      3215093 A1       9/2017
(Continued)

OTHER PUBLICATIONS

European Patent Office, Extended Search Report issued in EP22166750.4 dated Aug. 11, 2022.

*Primary Examiner* — Nicholas J. Weiss
*Assistant Examiner* — Brandon W. Levy
(74) *Attorney, Agent, or Firm* — Wood Herron & Evans LLP

(57) ABSTRACT

A textile for use as a reusable pad, e.g., a reusable incontinence pad, is provided that is intended to wick and retain moisture or liquid(s), such as bodily fluids (e.g., urine, blood, etc.), away from users of their incontinence pad. Moisture or liquid deposited on an upper surface of the incontinence pad is wicked through one or more layers of material included in the incontinence pad via an increasing capillary gradient using capillary forces. The incontinence pad relies on capillary forces to drive moisture from the incontinent person into the inner layer(s) of the incontinence pad, and leaving a top layer of the incontinence pad dry to the touch. A gradient of capillary size can be present in the incontinence pad in a direction away from the incontinent person, which accordingly encourages liquid to migrate away from the incontinent person and be desirably retained therein.

35 Claims, 7 Drawing Sheets

(52) U.S. Cl.
CPC ............... *A61F 2013/15276* (2013.01); *A61F 2013/530255* (2013.01); *A61F 2013/530897* (2013.01)

(58) Field of Classification Search
CPC .... A61F 2013/530897; A61F 13/15699; A61F 13/15731; A61F 13/51104; A61F 13/51121; A61F 13/5116; A61F 13/5123; A61F 13/51394; A61F 13/537; A61F 5/485; A61F 2013/53445; A61F 13/505; A61F 13/51405; A61F 13/5148; A61F 13/531; A61F 13/53747; A61F 2013/51409; A61F 2013/530226; A61F 2013/53721

See application file for complete search history.

(56) References Cited

U.S. PATENT DOCUMENTS

| | | | |
|---|---|---|---|
| 4,772,281 A | 9/1988 | Armstead | |
| 4,961,982 A | 10/1990 | Taylor | |
| 5,249,320 A | 10/1993 | Moretz et al. | |
| 5,290,269 A | 3/1994 | Heiman | |
| 5,334,177 A * | 8/1994 | Cohen | A61F 5/4401 604/358 |
| 5,486,167 A | 1/1996 | Dragoo et al. | |
| 5,522,809 A | 6/1996 | Larsonneur | |
| 5,562,648 A | 10/1996 | Peterson | |
| 5,735,145 A * | 4/1998 | Pernick | A61F 13/53 66/196 |
| 6,028,241 A | 2/2000 | Armstead | |
| 6,151,928 A | 11/2000 | Anyon et al. | |
| 7,361,803 B2 | 4/2008 | Miskie | |
| 2002/0099347 A1 * | 7/2002 | Chen | D21H 21/22 604/378 |
| 2007/0032767 A1 | 2/2007 | Horowitz | |
| 2007/0299383 A1 * | 12/2007 | Murphy | B32B 5/32 602/46 |
| 2010/0030170 A1 * | 2/2010 | Keller | A61F 13/8405 604/360 |
| 2010/0318054 A1 * | 12/2010 | Langdon | A61F 13/4902 604/385.24 |
| 2011/0092935 A1 | 4/2011 | Hann | |
| 2015/0083310 A1 * | 3/2015 | Wade | A61F 13/15601 156/167 |
| 2015/0250663 A1 * | 9/2015 | Wagner | A61F 13/512 604/378 |
| 2015/0282997 A1 * | 10/2015 | Arizti | A61F 13/51305 604/378 |
| 2016/0243522 A1 | 8/2016 | Rottger et al. | |
| 2016/0361206 A1 * | 12/2016 | Engelhardt | B32B 5/02 |
| 2017/0239107 A1 * | 8/2017 | Castrogiovanni | A61F 13/49413 |
| 2017/0258650 A1 * | 9/2017 | Rosati | D04H 1/42 |
| 2018/0179701 A1 | 6/2018 | Loyan et al. | |
| 2018/0229216 A1 * | 8/2018 | Smith | A61F 13/5116 |
| 2019/0110937 A1 | 4/2019 | Amy et al. | |

FOREIGN PATENT DOCUMENTS

| | | |
|---|---|---|
| GB | 1404453 A | 8/1975 |
| WO | 2016196006 A1 | 12/2016 |

* cited by examiner

REUSABLE PAD

TECHNICAL FIELD

The present invention relates to textiles with moisture wicking and absorbing properties and, more specifically, to such textiles for use as reusable incontinence pads and other similar items that are able to wick and retain moisture or liquid, such as bodily fluids, away from their users.

BACKGROUND

There are available in both the institutional and retail markets a variety of reusable and disposable products intended to wick moisture or liquid away from incontinent people or infants not yet toilet trained, for example. These products are commonly sold in a variety of configurations, fabrics, patterns, etc. as "incontinence pads", "diapers", "incontinence covers", "panty liners", and other similar descriptive designations. Regardless of fabrication or materials, whether quilted or unquilted, it is a ubiquitous feature of such existing products that they wick moisture away from the user of the product, leaving a layer of the product closest to the user to be relatively dry. This is an important aspect insofar as wetness on the layer closest to the user may result in discomfort, skin irritation, rash, or infection. Similarly, wetness, for example from overflow of inadequate incontinence pads, in the environment surrounding an incontinent person may be uncomfortable and/or unsanitary.

With respect to various drawbacks, it is understood that certain conventional reusable pads, such as incontinence pads, can be difficult to launder. For example, the materials used in the incontinence pads may not allow for the sufficient flow of wash water to pass through the textile layers to adequately clean the incontinence pad. Additionally, the construction of certain conventional incontinence pads can restrict the flow of air through the pad during drying, which could result in the pad remaining damp or require additional energy to completely dry the pad. Also, some conventional pads, particularly those with nonwoven absorbent layers, do not stand up well to repeated launderings. For example, the nonwoven structure of such absorbent layers tends to break down and become misshapen after being laundered repeatedly. Another problem with conventional reusable pads is that relatively thin liquid permeable face material can allow liquid captured in the absorbent layer to contact the skin of the user, with such prolonged exposure to dampness in the incontinence pad being unhygienic and potentially leading to the formation of bed sores and infection.

Accordingly, it is important from a hygienic as well as a comfort perspective that any reusable pad, e.g., a reusable incontinence pad, used by a person have capacity to hold sufficient bodily fluids discharged by the user, and also sufficiently encourage moisture to be wicked and retained away from the user, while also being durable enough to withstand repeated launderings, for example.

It would be desirable, therefore, to provide an improved reusable pad, such as a reusable incontinence pad (or other similar items), that can desirably wick and retain moisture (e.g. bodily fluids) away from users thereof that addresses one or more of the aforementioned and/or other drawbacks of conventional designs of reusable pads (e.g., reusable incontinence pads).

SUMMARY OF THE INVENTION

The present invention provides a reusable pad such as a reusable incontinence pad for use with an incontinent person that simultaneously provides both liquid transportation away from the incontinent person as well as liquid retention preventing liquid spread to an environment surrounding the incontinent person.

At least because the layer of the incontinence pad closest to the incontinent person is hydrophobic or anti-wicking, in one embodiment, the incontinence pad can rely on capillary forces to drive moisture or liquid from the incontinent person into the inner layer(s) of the incontinence pad, and leaving a top layer of the incontinence pad dry to the touch. A gradient of capillary size can be present in the incontinence pad in a direction away from the incontinent person, which accordingly encourages moisture or liquid to migrate away from the incontinent person and be desirably retained therein.

In one embodiment, a reusable pad, such as a reusable incontinence pad, is provided that includes a fabric top layer having a user-side surface for being situated adjacent a user and including a multifilament yarn, the top layer having a plurality of spaced apart openings formed therethrough and having a chemical treatment composition applied thereto. The chemical treatment composition includes one or more hydrophobic chemical compounds and/or one or more chemical compounds that impart hydrophobic properties to the top layer, wherein the chemical treatment composition provides a desired hydrophobicity to the top layer such that liquid from the user passes through the top layer via only the spaced apart openings. The reusable pad further includes a bottom barrier layer that includes an impermeable layer and a first wicking layer situated between the top layer and the bottom barrier layer. The first wicking layer includes a plurality of first wicking layer sub-layers including one or more plies of multifilament hydrophobic yarn with one sub-layer being adjacent the top layer and each of the plurality of sub-layers having a corresponding dpf value wherein the dpf values for each sub-layer increases when moving in a direction away from the top layer to provide a capillary gradient that promotes migration of liquid from the user in a direction away from the top layer.

In another embodiment, a reusable pad, such as a reusable incontinence pad, is provided that includes a fabric top layer having a user-side surface for being situated adjacent a user and including a polyester multifilament yarn that defines a polyester knit construction. The top layer has a plurality of spaced apart oval-shaped openings formed therethrough along a length and width of the top layer. The top layer further includes about 15 to 30 oval-shaped openings per square inch with the oval-shaped openings being from about 2.0 mm×1.0 mm to 7.0 mm×5.0 mm in size. The top layer also has a chemical treatment composition applied thereto, the chemical treatment composition including one or more hydrophobic chemical compounds and/or one or more chemical compounds that impart hydrophobic properties to the top layer, wherein the chemical treatment composition provides a desired hydrophobicity to the top layer such that liquid from the user passes through the top layer via only the spaced apart openings. The reusable pad further includes a bottom barrier layer that defines a multilayer laminate composite, which includes an outer scrim layer, an intermediate impermeable film layer, and an optional inner woven and/or knitted layer, and a first wicking layer situated below and adjacent the top layer. The first wicking layer includes a first wicking sub-layer situated adjacent the top layer, a sub-layer of tuck yarns, and a second wicking sub-layer. The sub-layer of tuck yarns are between and connect the first and second wicking sub-layers. The first wicking sub-layer includes one or more plies of multifilament hydrophobic yarn and has a first dpf value, the sub-layer of tuck yarns includes one or more plies of multifilament hydrophobic yarn and has a second dpf value, and the second wicking sub-layer includes one or more plies of multifilament hydrophobic yarn and has a third dpf value. The first dpf value is smaller than the second dpf value with the second dpf value being smaller than the third dpf to provide a capillary gradient that promotes migration of liquid from the user in a direction away from the top layer and towards the second wicking sub-layer. The reusable pad also includes a second wicking layer situated between the barrier layer and the first wicking layer. The second wicking layer includes one or more plies of multifilament hydrophobic yarn and having a dpf value greater than or equal to the first dpf value. And the woven top layer, the first wicking layer, and the second wicking layer are quilted together via a hydrophobic yarn.

In another embodiment, a method of making a reusable pad, such as a reusable incontinence pad, that is able to wick and retain liquid away from a user, is provided. The method includes layering a plurality of desirably sized layers and securing the layers together to form the reusable pad. The plurality of desirably sized layers include a fabric top layer having a user-side surface for being situated adjacent a user and including a multifilament yarn, The top layer has a plurality of spaced apart openings formed therethrough. The layers further include a bottom barrier layer that includes an impermeable layer and a first wicking layer situated between the top layer and the bottom barrier layer. The first wicking layer includes a plurality of first wicking layer sub-layers including one or more plies of multifilament hydrophobic yarn with one sub-layer being adjacent the top layer and each of the plurality of sub-layers having a corresponding dpf value wherein the dpf values for each sub-layer increases when moving in a direction away from the top layer to provide a capillary gradient that promotes migration of liquid from the user in a direction away from the top layer. The first wicking layer wicks liquid away from the user through the openings in the top layer. The method further includes prior to securing the layers together, applying a chemical treatment composition to the top layer. The chemical treatment composition includes one or more hydrophobic chemical compounds and/or one or more chemical compounds that impart hydrophobic properties to the top layer, wherein the chemical treatment composition provides a desired hydrophobicity to the top layer such that liquid from the user passes through the top layer via only the spaced apart openings.

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention. The components in the figures are not necessarily to scale. Moreover, in the figures, like-referenced numerals designate corresponding parts throughout the different views.

DETAILED DESCRIPTION

Any numerical ranges specified throughout the specification can include the endpoints of the range unless otherwise indicated. Furthermore, the ranges can include all values between the endpoints of the ranges unless otherwise indicated.

Figure 1:
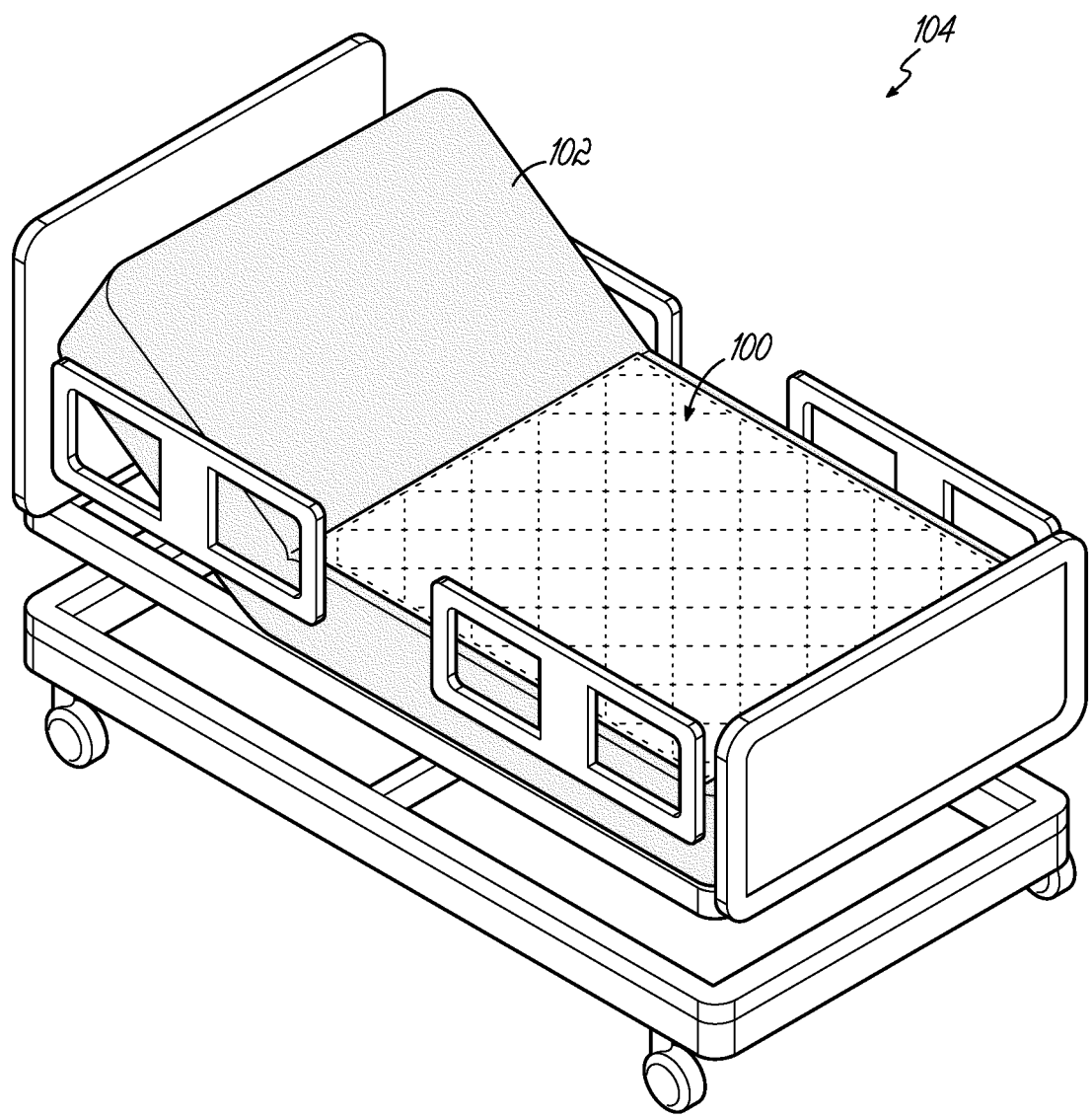
FIG. 1 is a perspective view of an adjustable medical bed including a reusable incontinence pad situated thereon in accordance with an embodiment of the invention.

FIG. 1 shows a reusable pad, such as a reusable incontinence pad 100, in accordance with an embodiment of the invention that can be placed, for example, on top of a bottom section of a mattress 102 of an adjustable medical bed 104. Here, the incontinence pad 100 is intended to be situated between the mattress 102 (and bedding thereon) and a person situated atop the mattress 102 and can protect the user as well as the mattress 102 (and its bedding) from contact with and/or penetration by liquid(s) such as bodily fluids (e.g., urine, blood, etc.) from the user. The incontinence pad 100 can include multiple layers of material that, when combined, help wick moisture away from the user of the incontinence pad 100 and retain the wicked moisture within an interior of the incontinence pad 100. The incontinence pad 100 can help protect the user from wetness and skin irritation and help prevent infection from bodily fluids, is durable enough to withstand repeated launderings, and is comfortable to the user, as further addressed below.

The reusable incontinence pad 100 of FIG. 1 is shown as a quilted composite sheet, yet, it should be understood that the incontinence pad 100, in certain embodiments, can be non-quilted and/or provided as a fitted sheet or situated thereunder or as a product that is designed to fit around the mattress 102, and may optionally be secured about the mattress 102. And while the incontinence pad 100 generally could be made from one or more layers of a woven, non-woven, knitted textile material, or combinations thereof and any number of suitable fibers or yarns, e.g., all-natural or synthetic fibers, or a blend or combination of natural and synthetic fibers and yarns may be employed to produce the incontinence pad 100, specific embodiments are discussed in detail hereinbelow. Also, any suitable techniques and equipment, including woven, knit, or non-woven fabric formation equipment and methods, likewise, may be employed, as may be known in the art, to produce the incontinence pad 100 and its layers. In one example, the incontinence pad 100 does not include any films or laminations as an outer layer in direct contact with a user. The incontinence pad 100 also can be manufactured to fit all mattress shapes and sizes. In other examples, the incontinence pad 100 can be manufactured and placed in, used as, or coupled to, an article such as an adult or infant diaper or, for example, a liner for a panty.

It is further contemplated that the reusable incontinence pads described herein may be manufactured, as desired, to retain varying amounts of liquids, such as bodily fluid(s). Incontinence pads manufactured to retain a relatively high volume of bodily fluid may be designed as larger pads such as used to protect bedding and mattresses, as shown in FIG. 1. In one example, the retention or insult volume of relatively high volume incontinence pads may be from 100 mL to 1200 mL. In another example, the retention or insult volume of the relatively high volume incontinence pads may be from 200 mL to 1000 mL. In yet another example, the retention or insult volume of the relatively high volume incontinence pads may be from 200 mL to 800 mL. In still another example, the retention or insult volume of the relatively high volume incontinence pads may be from 200 mL to 400 mL. The relatively high volume pads generally are designed, for example, to retain urine, feces, blood, or other bodily fluids. In large part, due to the volume of liquid to be retained by a high volume incontinence pad, these pads tend to be larger in size and may be, for example, about 30×30 inches in size or more. Alternatively, the incontinence pads described herein may be manufactured, as desired, to retain a relatively low(er) volume of bodily fluid. These relatively low volume pads may be worn by individuals and can be designed generally to retain urine from incontinence or blood for feminine hygiene, for example. In one example, the relatively low volume pads may retain from 5 mL to 200 mL. In another example, the relatively low volume pads may retain from 10 mL to 200 mL. In another example, the relatively low volume pads may retain from 20 mL to 100 mL. However, it is contemplated that any of the incontinence pads described herein may have a retention volume of anywhere from about 5 mL to 1200 mL. In large part, due to the volume of liquid to be retained by a low volume incontinence pad, these pads tend to be smaller in size and may be, for example, about 6×8 inches in size or less and can be hourglass shaped. In another example, the outer surface of the incontinence pad 100 that comes into contact with a user should be dry to the touch in about 60 seconds after a void or insult, i.e., after being exposed to liquid(s), such as bodily fluids (e.g., urine). In another example, the outer surface of the incontinence pad 100 that comes into contact with a user should be dry to the touch in about 30 seconds after a void or insult. In another example, the outer surface of the incontinence pad 100 that comes into contact with a user should be dry to the touch in less than 5 seconds after a void or insult.

The reusable incontinence pads of the present invention are intended to be washable either in commercial or home machines and able to withstand multiple launderings and, thus, reused multiple times. In one example, the reusable incontinence pads may be washed up to at least 50 times or cycles with drying times being about 45 minutes or less using a temperature of 160° F. to 180° F. In another example, the reusable incontinence pads may be washed up to at least 100 times or cycles with drying times being about 45 minutes or less using a temperature of 160° F. to 180° F. The reusable incontinence pads also may be treated, as is known in the art, to impart anti-microbial properties and other desired/desirable properties.

Figure 2:
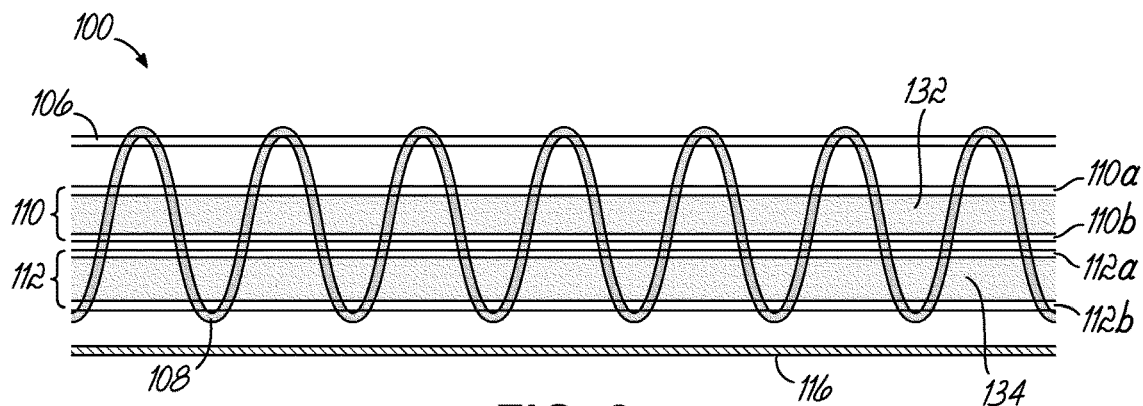
FIG. 2 is a partial cross-sectional view of the reusable incontinence pad of FIG. 1 in accordance with an embodiment of the invention.

With specific reference now to FIG. 2, a partial cross-sectional view of the reusable incontinence pad 100 of FIG. 1 is shown, which is a relatively high volume incontinence pad, and includes a top layer 106, wicking layers 110, 112, a barrier layer 116, and a quilting yarn 108. While the layers 106, 110, 112, 116 are generally depicted as having spacing therebetween, it should be understood that a layer may be directly adjacent to and/or in contact with its neighboring layers, particularly when the incontinence pad 100 is in use.

The top layer 106 of the incontinence pad 100 can include a hydrophobic or anti-wicking material that can help prevent moisture from permeating therethrough. In one example, the top layer 106 may be a woven substrate of a monofilament hydrophobic (or anti-wicking) yarn such as a polyester yarn (polyethylene terephthalate (PET)), polytetrafluoroethylene (PTFE) yarn, polypropylene (PP), or the like. Due to the use or presence of monofilament yarn, the top layer 106 has little to no capillary action. In one example, the woven substrate of the top layer 106 can be composed of from 20 denier to 200 denier hydrophobic yarn so as to provide a desirable hand or feel for the user. In another example, the woven substrate can be from 50 denier to 100 denier hydrophobic yarn. In one example, the top layer 106 defines a low coefficient of friction, is quiet, and can be soft to the touch.

Ordinarily, if moisture or liquid were to be present on the user-side surface of the top layer 106, the moisture would not permeate through the top layer 106 of the incontinence pad 100 due, in large part, to the cohesive forces of the liquid(s) being unable to penetrate the top layer 106 and the lack of capillary presence or action of the monofilament layer. However, at least due to the presence of the wicking layer 110 coming in contact with the top layer 106, particularly when a user is positioned on the incontinence pad 100, moisture or liquid is able to wick through the hydrophobic top layer 106 into the wicking layers 110, 112 of the incontinence pad 100 by capillary forces, as further explained below. Openings created in the layers 106, 110, 112 by quilting using the quilting yarn 108 is understood to assist in the capillary transport or wicking action of the wicking layer(s) 110, 112 below the top layer 106.

Capillary size is defined by the denier per filament (dpf), which is the size of an individual filament, is directly related to total denier and the total filaments in the material used in the wicking layers described herein. That is, dpf can be calculated by taking the yarn denier and dividing it by the number of filaments in the yarn bundle. The greater the dpf of wicking layers described herein, the greater the capillary size of the wicking layer. In addition, the greater the dpf of a wicking layer relative to an adjacent layer, the greater the tendency to accept moisture from that adjacent layer.

With continuing reference now to FIG. 2, the wicking layers 110, 112 can each include sub-layers. More specifically, the wicking layer 110 can include wicking layers 110a and 110b with tuck yarns 132 therebetween. And wicking layer 112, similarly, can include wicking layers 112a and 112b with tuck yarns 134 therebetween. The wicking layer 110 may have a smaller capillary size than wicking layer 112 or, in other embodiments, be close to or the same as wicking layer 112. Generally speaking, a capillary gradient exists in the direction away from the top layer 106 such that there can be increasing capillary size in the wicking layers 110, 112 of the incontinence pad 100. The increasing gradient of capillary size is a driving force for the movement of moisture by capillary forces away from the user of the incontinence pad 100. In this embodiment, a similar gradient exists within each of the wicking layers 110, 112. That is, wicking layer 110a has a smaller capillary size (or smaller dpf) than wicking layer 110b and wicking layer 112a has a smaller capillary size (or smaller dpf) than wicking layer 112b, but the capillary size (or dpf) of wicking layer 110a and 110b may be about the same or the same as the capillary size (or dpf) of the wicking layer 112a and 112b, for example.

In one embodiment, the wicking layer 110 can include a woven and/or knitted layer(s) of material that can come into contact or be in communication with the top layer 106 and be configured to promote wicking of moisture from the user-side surface of the top layer 106 into the wicking layer 110. As indicated above, the wicking layer 110 can be subdivided into wicking layers 110a, 110b with tuck yarns 132 situated therebetween and connecting the wicking layers 110a, 110b, by means and methods known in the art.

The wicking layer 110a can be a knit layer that can include one or more different types of hydrophobic yarns, such as nylon, polyester, and the like. In one embodiment, the wicking layer 110a can include one or more plies of multifilament material. Filaments included in each of the plies of the wicking layer 110a may be the same material or different materials within the plies as well as among the plies. The wicking layer 110a can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The wicking layer 110a can have a capillary size or dpf from about 0.3 to 5. In another example, the wicking layer 110a can have a capillary size or dpf from about 1 to 5. In another example, the wicking layer 110a can have a capillary size or dpf from about 1 to 4, about 1 to 3, or about 1 to 2. In another example, the wicking layer 110a can have a dpf of less than 1 or greater than 5. In one embodiment, the wicking layer 110a can be composed of a combination of 2-ply, 70 denier, and 34 filament nylon and 1 ply, 50 denier, and 36 filament polyester.

Wicking layer 110 further includes a knit layer of tuck yarns 132 situated between and connecting wicking layer 110a and wicking layer 110b. The tuck yarns 132 are configured to promote the migration of moisture from the wicking layer 110a away from the user of the incontinence pad 100 and can have a larger capillary size (or dpf) than wicking layer 110a. In one embodiment, the tuck yarns 132 can be defined by a knit layer of one or more types of hydrophobic yarns, such as polyester, elasterell-p, nylon, and the like. In one embodiment, the tuck yarns 132 can include one or more plies of multifilament material. Filaments included in each of the plies of the tuck yarns 132 may be the same material or different materials within the plies as well as among the plies. The tuck yarns 132 can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The tuck yarns 132 can have a capillary size or dpf from about 0.3 to 5. In another example, the tuck yarns 132 can have a capillary size or dpf from about 1 to 5. In another example, the tuck yarns 132 can have a capillary size or dpf from about 1 to 4, about 1 to 3, or about 1 to 2. In another example, the tuck yarns 132 can have a dpf of less than 1 or greater than 5. In one embodiment, the tuck yarns 132 can be composed of a combination of 1 ply, 100 denier, 36 filament polyester and 1 ply, 150 denier, 68 filament elasterell-p.

Wicking layer 110 further includes wicking layer 110b. In one example, the wicking layer 110b can be a knit layer having one or more different types of hydrophobic yarns, such as nylon, polyester, and the like. In one embodiment, the wicking layer 110b can include one or more plies of multifilament material. Filaments included in each of the plies of the wicking layer 110b may be the same material or different materials within the plies as well as among the plies. The wicking layer 110b can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The wicking layer 110b can have a capillary size or dpf from about 0.3 to 5. In another example, the wicking layer 110b can have a capillary size or dpf from about 1 to 5. In another example, the wicking layer 110b can have a capillary size or dpf from about 1 to 4, about 1 to 3, or about 1 to 2. In another example, the wicking layer 110b can have a dpf of less than 1 or greater than 5. The wicking layer 110b can be configured to promote the migration of moisture from the tuck yarns 132 and can have a larger capillary size thereof. In one embodiment, wicking layer 110b can be a multifilament knit layer composed of polyester. In another embodiment, the wicking layer 110b can be composed of a 1 ply, 150 denier, 68 filament polyester.

With continuing reference to FIG. 2, wicking layer 112 can include a woven and/or knitted layer(s) of material configured to promote wicking of moisture from the wicking layer 110 into the wicking layer 112. The wicking layer 112, like wicking layer 110, can be subdivided into wicking layers 112a, 112b with a layer of tuck yarns 134 that are situated therebetween and connecting the wicking layers 112a, 112b, by means and methods known in the art.

The wicking layer 112a can be a knit layer that can include one or more different types of hydrophobic yarns, such as nylon, polyester, and the like. In one embodiment, the wicking layer 112a can include one or more plies of multifilament material. Filaments included in each of the plies of the wicking layer 112a may be the same material or different materials within the plies as well as among the plies. The wicking layer 112a can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The wicking layer 112a can have a capillary size or dpf from about 0.3 to 5. In another example, the wicking layer 110a can have a capillary size or dpf from about 1 to 5. In another example, the wicking layer 112a can have a capillary size or dpf from about 1 to 4, about 1 to 3, or about 1 to 2. In another example, the wicking layer 112a can have a dpf of less than 1 or greater than 5. In one embodiment, the wicking layer 112a can be composed of a combination of 2-ply, 70 denier, and 34 filament nylon and 1 ply, 50 denier, and 36 filament polyester.

Wicking layer 112 further includes a knit layer of tuck yarns 134 situated between and connecting wicking layer 112a and wicking layer 112b. The tuck yarns 134 are configured to promote the migration of moisture from the wicking layer 112a, and still yet further away from the user of the incontinence pad 100, and can have a larger capillary size than wicking layer 112a. In an embodiment, the tuck yarns 134 can be defined by a knit layer of one or more types of hydrophobic yarns, such as polyester, elasterell-p, nylon, and the like. In one embodiment, the tuck yarns 134 can include one or more plies of multifilament material. Filaments included in each of the plies of the tuck yarns 134 may be the same material or different materials within the plies as well as among the plies. The tuck yarns 134 can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The tuck yarns 134 can have a capillary size or dpf from about 0.3 to 5. In another example, the tuck yarns 134 can have a capillary size or dpf from about 1 to 5. In another example, the tuck yarns 134 can have a capillary size or dpf from about 1 to 4, about 1 to 3, or about 1 to 2. In another example, the tuck yarns 134 can have a dpf of less than 1 or greater than 5. In one embodiment, the tuck yarns 134 can be composed of a combination of 1 ply, 100 denier, 36 filament polyester and 1 ply, 150 denier, 68 filament elasterell-p.

Wicking layer 112 further includes wicking layer 112b. In one example, the wicking layer 112b can be a knit layer having one or more different types of hydrophobic yarns, such as nylon, polyester, and the like. In one embodiment, the wicking layer 112b can include one or more plies of multifilament material. Filaments included in each of the plies of the wicking layer 112b may be the same material or different materials within the plies as well as among the plies. The wicking layer 112b can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The wicking layer 112b can have a capillary size or dpf from about 0.3 to 5. In another example, the wicking layer 112b can have a capillary size or dpf from about 1 to 5. In another example, the wicking layer 112b can have a capillary size or dpf about 1 to 4, about 1 to 3, or about 1 to 2. In another example, the wicking layer 112b can have a dpf of less than 1 or greater than 5. The wicking layer 112b can be configured to promote the migration of moisture from the tuck yarns 134 and can have a larger capillary size thereof. In one embodiment, wicking layer 112b can be a multifilament knit layer composed of polyester. In another embodiment, the wicking layer 112b is composed of a 1 ply, 150 denier, 68 filament polyester.

The quilting yarn 108 is a yarn that connects the top layer 106 to the wicking layers 110, 112 via quilting means and methods known in the art. The quilting yarn 108 may be any suitable natural or synthetic yarn. In one example, the yarn 108 is a hydrophobic yarn, such as polyester, nylon, and the like. In one embodiment, the yarn is 100% polyester spun yarn. The yarn may be chemically treated to enhance the wicking of moisture. The quilting yarn 108 may be arranged in a quilting pattern in the incontinence pad 100.

The barrier layer 116 is a layer that prevents moisture or liquid accumulated in the incontinence pad 100 from escaping and spilling into the surrounding environment outside of the incontinence pad 100. In other words, the barrier layer 116 can be impermeable and/or waterproof. The barrier layer 116 can contact the wicking layer 112. The barrier layer 116 may include a polyester layer coated with a polyvinyl chloride (PVC) or other hydrophobic, impermeable material, such as a laminated polyurethane. The PVC coating provides significant hydrophobic/barrier properties such that moisture collected by the incontinence pad 100 is retained within the incontinence pad 100. The barrier layer 116 can be formed by means and methods known in the art, such as by heat pressing together the layers. The edges of the incontinence pad 100 can be hemmed (FIG. 1), as is known in the art, to further secure the top layer 106 to the wicking layers 110, 112 and the barrier layer 116.

Figure 2A:
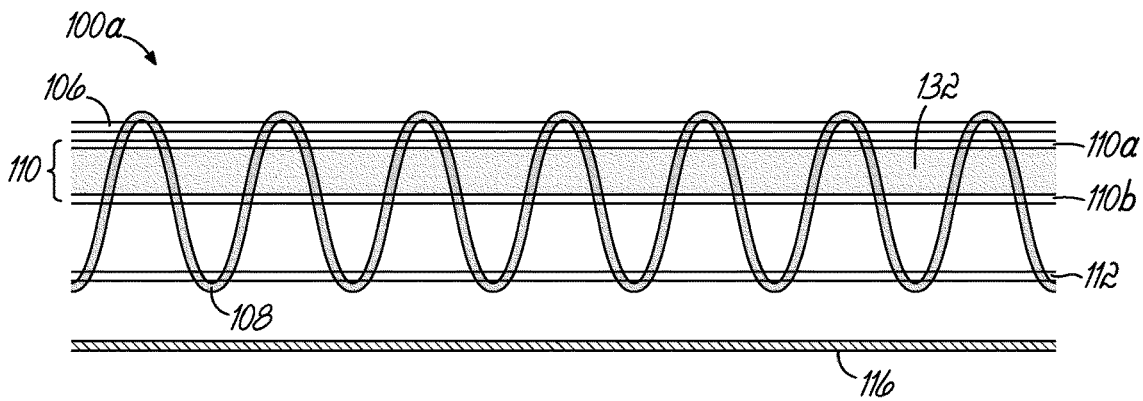
FIG. 2A is a partial cross-sectional view of a variation of the reusable incontinence pad of FIG. 2 in accordance with an embodiment of the invention.

With reference now to FIG. 2A, a cross-section of a reusable incontinence pad 100a in accordance with another embodiment of the invention is shown, which is a variation of the reusable incontinence pad 100 of FIG. 2, with the exception that the wicking layer 112 with its wicking layers 112a, 112b, and layer of tuck yarns 134 has been replaced with a single wicking layer 112. Here, the wicking layer 112 can include a woven and/or knitted layer of material that can come into contact with the wicking layer 110 and, more specifically, wicking layer 110b, and be configured to promote wicking of moisture from the wicking layer 110 therein.

The wicking layer 112 can be a knit layer that can include one or more different types of hydrophobic yarns, such as nylon, polyester, and the like. In one embodiment, the wicking layer 112 can include one or more plies of multifilament material. Filaments included in each of the plies of the wicking layer 112 may be the same material or different materials within the plies as well as among the plies. The wicking layer 112 can be composed of yarns having from 20 denier to 500 denier. In another example, the yarns can have from 20 denier to 400 denier. In another example, the wicking layer 112 can be composed of yarns having from 20 denier to 300 denier. In another example, the yarns can have from 50 denier to 300 denier. The wicking layer 112 can have a capillary size or dpf from about 0.3 to 5. In another example, the wicking layer 112 can have a capillary size or dpf from about 1 to 5. In another example, the wicking layer 112 can have a capillary size or dpf from about 1 to 4, about 1 to 3, or about 1 to 2. In another example, the wicking layer 112 can have a dpf of less than 1 or greater than 5. In one embodiment, the wicking layer 112 can be composed of 1-ply, 150 denier, and 34 filaments polyester having a 4.4 dpf.

In another embodiment and with continued reference to FIG. 2A, the wicking layer 110 with its wicking layers 110a, 110b, and layer of tuck yarns 132 can include only a single type of knit yarn in each layer 110a, 110b, 132 that provides for a clearly defined and increasing capillary gradient therein. More specifically, wicking layer 110a, 110b, and the layer of tuck yarns 132 can be a knit layer that can include one type of hydrophobic yarn, such as nylon, polyester, and the like. In one example, wicking layer 110a, 110b, and the layer of tuck yarns 132 can include one or more plies of multifilament material. The wicking layer 110a, 110b, and the layer of tuck yarns 132 can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The wicking layer 110a, 110b, and the layer of tuck yarns 132 can have a capillary size or dpf from about 0.3 to 5. In another example, the wicking layer 110a, 110b, and the layer of tuck yarns 132 can have a capillary size or dpf from about 1 to 5. In another example, the wicking layer 110a, 110b, and the layer of tuck yarns 132 can have a capillary size or dpf from about 1 to 4, or about 1 to 3, or about 1 to 2. In another example, the wicking layer 110a, 110b, and the layer of tuck yarns 132 can have a dpf of less than 1 or greater than 5. In one specific embodiment, the wicking layer 110a can be composed of 1 ply, 75 denier, and 72 filament polyester having a 1.04 dpf, the tuck yarns 132 can be composed of a 1-ply, 100 denier, and 36 filament polyester with a 2.8 dpf, and the wicking layer 110b can be composed of a 2-ply, 150 denier, 34 filament polyester having 4.4 dpf.

Figure 3:
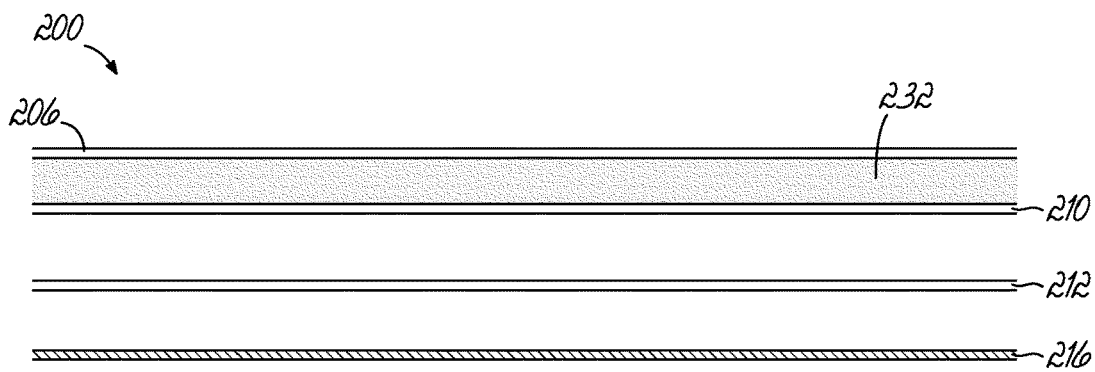
FIG. 3 is a cross-sectional view of a reusable incontinence pad in accordance with another embodiment of the invention.

With reference now to FIG. 3, a cross-section of a reusable incontinence pad 200 in accordance with another embodiment of the invention is shown. The incontinence pad 200 here is similar to the incontinence pad 100 of FIG. 2, with the exception that the incontinence pad 200 omits an equivalent wicking layer 110a so that a layer of tuck yarns 232 connects top layer 206 directly with wicking layer 210. As a result, quilting is unnecessary and there is no equivalent quilting yarn 108. In view thereof, the incontinence pad 200 shown in FIG. 3 may be less inclined to bunch together during use, at least due to the lack of quilting in incontinence pad 200. In addition, the wicking layer 112 of the incontinence pad 100 of FIG. 2 with its wicking layers 112a, 112b, and layer of tuck yarns 134 has been replaced with a single wicking layer 212, like that of FIG. 2A. Accordingly, the incontinence pad 200, as shown in FIG. 3, includes a top layer 206, wicking layer 210, and a layer of tuck yarns 232 therebetween connecting the top layer 206 and the wicking layer 210, along with a single wicking layer 212, and a barrier layer 216. The edges of the incontinence pad 200 can be hemmed, as is known in the art, to further secure the top layer 206, tuck yarns 232, and wicking layer 210 with the wicking layer 212 and the barrier layer 216.

By further comparison to the incontinence pad of FIG. 3, the top layer 206 can include monofilament yarn as discussed above with respect to the reusable incontinence pad 100 of FIG. 2, and the yarns in tuck yarns 232, wicking layer 210, and wicking layer 212 have been specifically selected to provide an increasing capillary gradient in the reusable incontinence pad 200. For example, the dpf can increase in size between layers as liquid moves from the tuck yarns 232, to the wicking layer 210, and finally to the wicking layer 212. Here, wicking layer 210, the layer of tuck yarns 232, and wicking layer 212 can be a knit layer that can include one type of hydrophobic yarn, such as nylon, polyester, and the like. In one embodiment, wicking layer 210, 212, and the layer of tuck yarns 232 can include one or more plies of multifilament material. The wicking layer 210, 212, and the layer of tuck yarns 232 can be composed of yarns having from 20 denier to 500 denier. In another example, the yarns can have from 20 denier to 400 denier. In another example, the yarns can have from 20 to 300 denier. In another example, the yarns can have from 50 denier to 300 denier. The wicking layer 210, 212, and the layer of tuck yarns 232 can have a capillary size or dpf from about 0.3 to 5. In another example, the wicking layer 210, 212, and the layer of tuck yarns 232 can have a capillary size or dpf from about 1 to 5. In another example, the wicking layer 210, 212, and the layer of tuck yarns 232 can have a capillary size or dpf from about 1 to 4, or about 1 to 3, or about 1 to 2. In another example, the wicking layer 210, 212, and the layer of tuck yarns 232 can have a dpf of less than 1 or greater than 5. In one embodiment, the top layer 206 can be composed of 50 denier monofilament polyester, the tuck yarns 232 can be composed of a 1-ply, 75 denier, and 72 filament polyester with a 1.1 dpf, the wicking layer 210 can be composed of 1 ply, 100 denier, and 36 filament polyester having a 2.8 dpf, and the wicking layer 212 can be composed of a 2-ply, 150 denier, 34 filament polyester having 4.4 dpf. The remaining layers, such as barrier layer 216 is as discussed above with respect to the incontinence pad 100 of FIG. 2.

Figure 4:
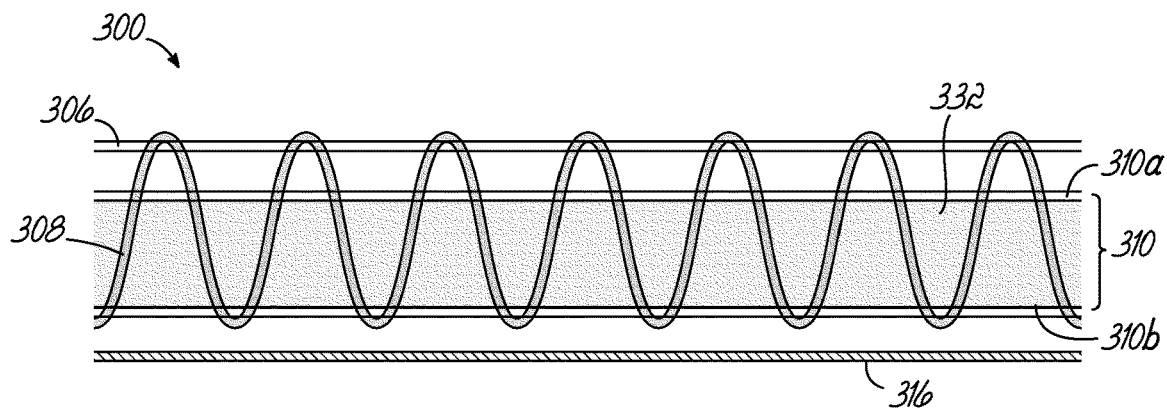
FIG. 4 is a cross-sectional view of a reusable incontinence pad in accordance with another embodiment of the invention.

With reference now to FIG. 4, a cross-sectional view of a reusable incontinence pad 300 in accordance with another embodiment of the invention is shown. The incontinence pad 300 here is a relatively low volume incontinence pad as compared to the large(r) volume incontinence pad of FIG. 2 (or incontinence pad 100a of FIG. 2A), for example. Despite the smaller volume characteristics, the reusable incontinence pad 300 is similar to the reusable incontinence pad 100 of FIG. 2, with the exception that the incontinence pad 300 completely omits an equivalent wicking layer 112. And by further comparison to the incontinence pad of FIG. 2, the yarns in wicking layers 310a, 310b, and tuck yarns 332 have been specifically selected to provide an increasing capillary gradient in the incontinence pad 300. For example, the dpf can increase in size between layers as liquid moves from the wicking layer 310a, to the layer of tuck yarns 332, and finally to the wicking layer 310b. Accordingly, the incontinence pad 300, as shown in FIG. 4, includes a top layer 306, wicking layer 310 having wicking layers 310a and 310b and a layer of tuck yarns 332 therebetween connecting wicking layers 310a and 310b, and a barrier layer 316. Here, the barrier layer 316 can come into direct contact with the wicking layer 310b.

Specifically concerning the wicking layer 310, the wicking layers 310a, 310b and the layer of tuck yarns 332 can be a knit layer that can include one type of hydrophobic yarn, such as nylon, polyester, and the like. In one embodiment, the wicking layers 310a, 310b, and the layer of tuck yarns 332 can include one or more plies of multifilament material. The wicking layers 310a, 310b, and the layer of tuck yarns 332 can be composed of yarns having from 20 denier to 500 denier. In another example, the yarns can have from 20 denier to 400 denier. In another example, the yarns can have from 20 to 300 denier. In another example, the yarns can have from 50 denier to 300 denier. The wicking layers 310a, 310b, and the layer of tuck yarns 332 can have a capillary size or dpf from about 0.3 to 5. In another example, the wicking layers 310a, 310b, and the layer of tuck yarns 332 can have a capillary size or dpf from about 1 to 5. In another example, the wicking layers 310a, 310b, and the layer of tuck yarns 332 can have a capillary size or dpf from about 1 to 4, or about 1 to 3, or about 1 to 2. In another example, the wicking layers 310a, 310b, and the layer of tuck yarns 332 can have a dpf of less than 1 or greater than 5. In one embodiment, the wicking layer 310a can be composed of 1 ply, 50 denier, and 36 filament polyester having a 1.4 dpf, the tuck yarns 332 can be composed of a 1-ply, 100 denier, and 36 filament polyester with a 2.8 dpf, and the wicking layer 310b can be composed of a 1-ply, 40 denier, 13 filament nylon with a 3.1 dpf or a 1-ply, 150 denier, 34 filament polyester having a 4.4 dpf. The remaining layers, including the top layer 306 and barrier layer 316, as well as the quilting yarn 308, are as discussed above with respect to the incontinence pad 100 of FIG. 2 (or incontinence pad 100a of FIG. 2A).

The edges of the incontinence pad 300 can be hemmed, as is known in the art, to further secure the top layer 306 to the wicking layer 310, and the barrier layer 316.

Figure 5:
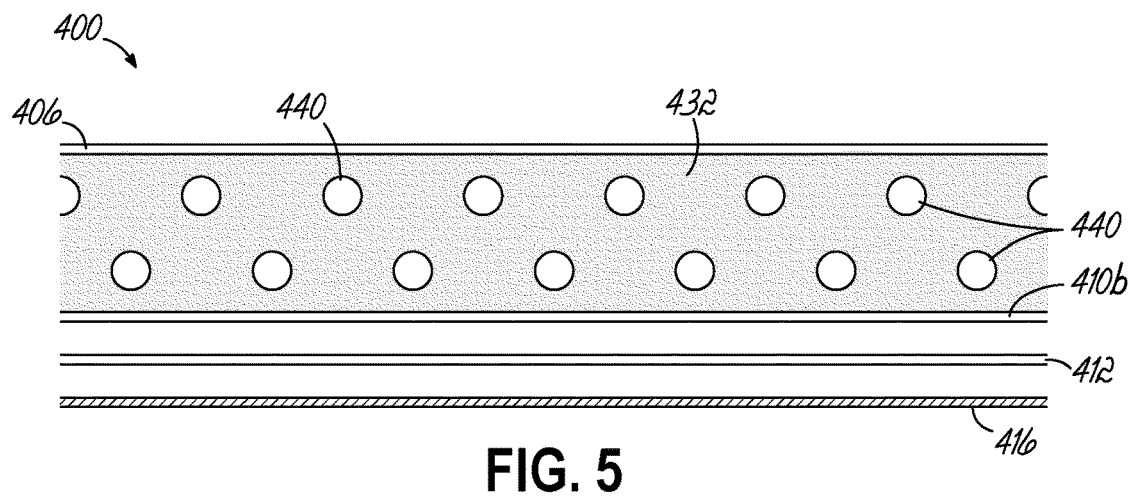
FIG. 5 is a cross-sectional view of a reusable incontinence pad in accordance with another embodiment of the invention.

FIG. 5 shows a cross-sectional view of a low volume, reusable, unquilted incontinence pad 400 in accordance with another embodiment of the invention that is similar in many respects to the high volume and unquilted reusable incontinence pad 200 of FIG. 3 insofar as the reusable incontinence pad 400 omits an equivalent wicking layer 110a (See FIG. 2) so that a layer of tuck yarns 432 connects top layer 406 directly with wicking layer 410b. In addition, there also is a single wicking layer 412. That is, there are no equivalent wicking layers 112a, 112b or a layer of tuck yarns 134 (FIG. 2). As a result, quilting is unnecessary and there is no equivalent quilting yarn 108 (FIG. 2). In view thereof, the incontinence pad 400 shown in FIG. 5, like that of FIG. 3, may be less inclined to bunch together during use, at least due to the lack of quilting. The incontinence pad 400 additionally includes (weft) insertion yarns 440 within the area of the tuck yarns 432 and between the top layer 406 and wicking layer 410b. The insertion yarns 440 can include a plurality of filaments that run in the weft direction of the incontinence pad 400. Alternatively, the weft insertion yarns 440 may run in the warp direction of the incontinence pad 400. Accordingly, the incontinence pad 400, as shown in FIG. 5, includes a top layer 406, wicking layer 410b, and a layer of tuck yarns 432 therebetween connecting the top layer 406 and the wicking layer 410b, along with multiple insertion yarns 440, a single wicking layer 412, and a barrier layer 416. In other embodiments, the wicking layer 412 may include more than one wicking layers 412, such as two or more wicking layers 412 (not shown).

The insertion yarns 440 can include one or more plies of mono- or multifilament material. In one example, the insertion yarns are composed of one or more types of hydrophobic yarns, such as polyester, nylon, and the like. Filaments included in each of the plies thereof may be the same material or different materials within the plies as well as among the plies. The insertion yarns 440 can be composed of yarns having from 20 denier to 500 denier. In another example, the yarns can have from 20 denier to 400 denier. In another example, the yarns 440 can have from 20 denier to 300 denier. In another example, the yarns 440 can have from 50 denier to 300 denier, or 50 denier to 150 denier. The insertion yarns 440 can have a capillary size or dpf from about 0.3 to 5. In another example, the insertion yarns 440 can have a capillary size or dpf from about 1 to 5. In another example, the insertion yarns 440 can have a capillary size or dpf from about 1 to 4, about 1 to 3, or about 1 to 2. In another example, the insertion yarns 440 can have a dpf of less than 1 or greater than 5. In one embodiment, the insertion yarns 440 can be composed of 1 ply, 50 denier, and 36 filaments polyester having a 1.4 dpf.

With further reference to FIG. 5 (and like the incontinence pad 200 of FIG. 3), the yarns in tuck yarns 432, wicking layer 410b, and wicking layer 412, as well as the insertion yarns 440, have been specifically selected to provide a generally increasing capillary gradient in the incontinence pad 400. For example, the dpf can increase in size between the layers/yarns as liquid moves from the top surface 406 to the wicking layer 412. Here, along with the insertion yarns 440, the wicking layer 410b, the layer of tuck yarns 432, and the wicking layer 412 can be a knit layer or composed of knit yarns that can include one type of hydrophobic yarn, such as nylon, polyester, and the like. In one embodiment, wicking layer 410b, insertion yarns 440, and the layer of tuck yarns 432, and wicking layer 412 can include one or more plies of mono- or multifilament material. The wicking layer 410b, 412, and the layer of tuck yarns 432 can be composed of yarns having from 20 denier to 500 denier. In another example, the yarns can have from 20 denier to 400 denier. In another example, the yarns can have from 20 to 300 denier. In another example, the yarns can have from 50 denier to 150 denier. The wicking layer 410b, insertion yarns 440, wicking layer 412, and the layer of tuck yarns 432 can have a capillary size or dpf from about 0.3 to 5. In another example, the wicking layer 410b, insertion yarns 440, wicking layer 412, and the layer of tuck yarns 432 can have a capillary size or dpf from about 1 to 5. In another example, the wicking layer 410b, insertion yarns 440, wicking layer 412, and the layer of tuck yarns 432 can have a capillary size or dpf from about 1 to 4, or about 1 to 3, or about 1 to 2. In another example, the wicking layer 410b, insertion yarns 440, wicking layer 412, and the layer of tuck yarns 432 can have a dpf of less than 1 or greater than 5. In one embodiment, top layer can be composed of monofilament polyester yarn, the tuck yarns 432 can be composed of a 1-ply, 50 denier, and 36 filament polyester with a 1.4 dpf or be a monofilament polyester yarn having 50 denier, the wicking layer 410b can be composed of 1 ply, 100 denier, and 36 filament polyester having a 2.8 dpf, the wicking layer 212 can be composed of a 1-ply, 150 denier, 34 filament polyester having 4.4 dpf, with the insertion yarns composed of a 1-ply, 50 denier, and 36 filament polyester with a 1.4 dpf.

The remaining layers, including the top layer 406 and barrier layer 416 are as discussed above with respect to the incontinence pad 100 of FIG. 2 (or incontinence pad 100a of FIG. 2A. The edges of the incontinence pad 400 can be hemmed, as is known in the art, to further secure the top layer 406, the wicking layer 410b, tuck yarns 432, wicking layer 412, and the barrier layer 416.

Figure 5A:
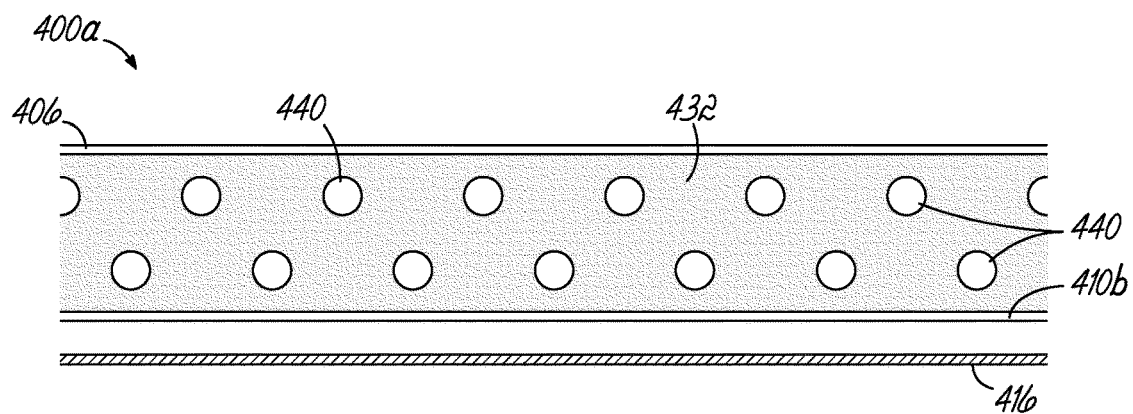
FIG. 5A is a cross-sectional view of a variation of the reusable incontinence pad of FIG. 5 in accordance with an embodiment of the invention.

With reference now to FIG. 5A, a cross-section of an unquilted reusable incontinence pad 400a in accordance with another embodiment of the invention is shown, which is a variation of the reusable incontinence pad 400 of FIG. 5 wherein the wicking layer 412 has been completely omitted from the incontinence pad 400a. To that end, the capillary sizes or dpf for certain of the yarns, such as the insertion yarns 440, and the yarns of the wicking layer 410b have been adjusted to provide a desirable capillary gradient in view of the removal of the wicking layer 412. While the remaining layers, including the top layer 406, wicking layer 410b, the layer of tuck yarns 432, the barrier layer 416, as well as the insertion yarns 440 generally are as discussed above with respect to the incontinence pad 400 of FIG. 5, in one example, the weft insertion yarns 440 can be composed of a 1-ply, 100 denier, and 96 filament polyester with a 1.1 dpf, the tuck yarns can be composed of a monofilament polyester yarn having 50 denier, and the wicking layer 410b can be composed of a 2-ply, 150 denier, and 34 filament polyester with a 4.4 dpf.

In another embodiment of the invention, the top layer 106, 206, 306, 406 of each reusable incontinence pad 100, 100a, 200, 300, 400, 400a can be a hydrophobic plastic film that can provide a desirable hand or feel for the user and that can help prevent moisture from permeating therethrough. The plastic film can have a low coefficient of friction, be quiet, and can be soft to the touch. In one example, the top layer 106, 206, 306, 406 is a flocked film, such as a flocked polyvinyl chloride (PVC) film, or is a 3d printed film, such as a 3d printed latex film. The film can be secured as part of the composite sheet as discussed above, such as via quilting or other securement means, for example.

Figure 6:
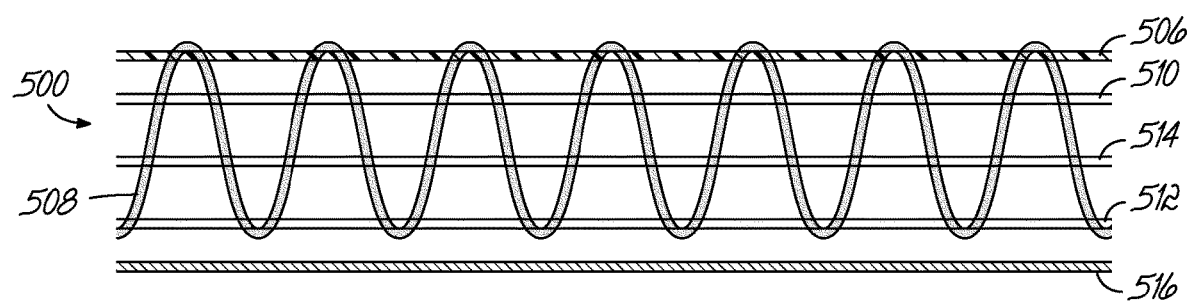
FIG. 6 is a cross-sectional view of a reusable incontinence pad in accordance with another embodiment of the invention.

With reference now to FIG. 6, a cross-section of a reusable incontinence pad 500 in accordance with another embodiment of the invention is shown. The reusable incontinence pad 500 here is similar to the reusable incontinence pad 100 of FIG. 2 in certain respects, with the exception that the top layer 506 is a hydrophobic plastic film, e.g., a flocked film, such as a flocked polyvinyl chloride (PVC) film, or a 3d printed film, such as a 3d printed latex film, and wicking layer 510 and 512 each define but a single wicking layer, with an optional intermediate absorbent layer 514 situated therebetween, which can include an absorbent terry layer (e.g., 100% cotton terry layer) to retain fluids/moisture within the incontinence pad 500. The wicking layers 510, 512 can be as described above and include a woven and/or knitted layer of material that can be configured to promote wicking of moisture within the incontinence pad 500 towards the intermediate layer 514 for retention of fluids therein. In one example, wicking layer 510 can be a woven substrate of a mono- or multifilament hydrophobic yarn such as a polyester yarn (polyethylene terephthalate (PET)), polytetrafluoroethylene (PTFE) yarn, polypropylene (PP), or the like, and wicking layer 512 can be a knit layer that can include one or more different types of hydrophobic yarns, such as nylon, polyester (e.g., PET), and the like. In another example, the wicking layer 510 can be a knit layer that can include one or more different types of hydrophobic yarns, such as nylon, polyester (e.g., PET), and the like, similar to wicking layer 512. In one example, the capillary size of wicking layer 510 may be about the same or the same as the capillary size of the wicking layer 512, for example.

Figure 7:
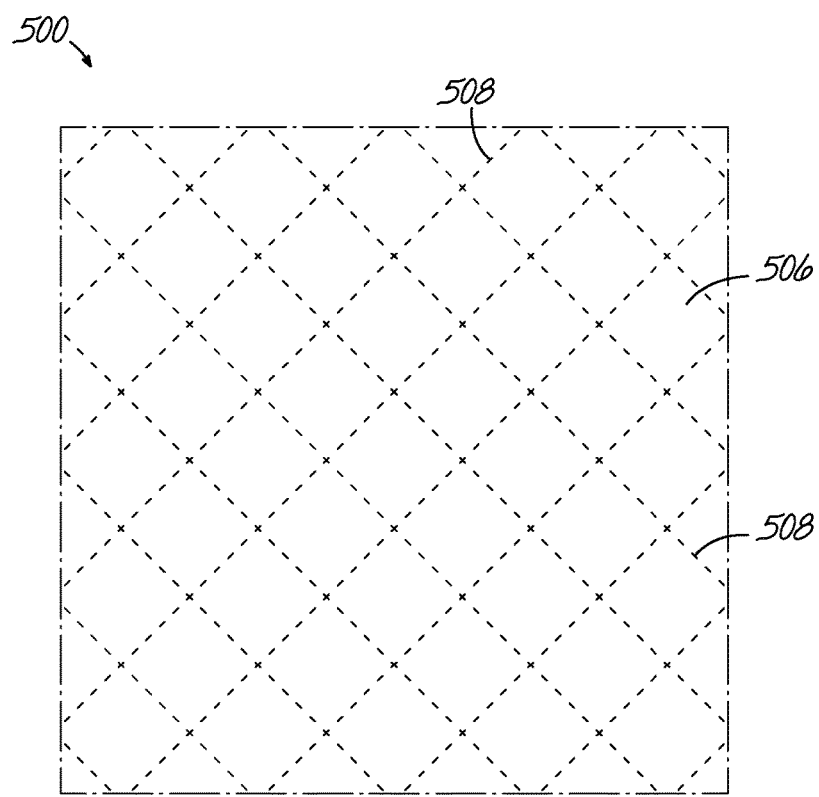
FIG. 7 is a top view of the reusable incontinence pad of FIG. 6 in accordance with an embodiment of the invention.

The reusable incontinence pad 500 of FIG. 6 further includes a barrier layer 516 and a quilting yarn 508, which can be as described above with respect to incontinence pad 100 shown in FIG. 2, and the edges of the incontinence pad 500 can be hemmed, as is known in the art, to further secure together the top layer 506, wicking layers 510, 512, intermediate layer 514, and the barrier layer 516. The quilting yarn 508, which may be chemically treated to promote wicking and moisture transport, connects the top layer 506 to the wicking layers 510, 512 and intermediate layer 514, such as via quilting means and methods known in the art. The yarn 508 can be a hydrophobic yarn, such as polyester, nylon, and the like. In one example, the yarn 508 is a 100% polyester yarn. Openings created in the layers 506, 510, 512, and 514 by quilting using the quilting yarn 508 are understood to assist in the capillary transport or wicking action of the wicking layer(s) 510, 512 below the top layer 506 to move moisture to the intermediate absorbent layer 514. The quilting yarn 508, as shown in FIG. 7, may be arranged in a desired quilting pattern in the incontinence pad 500 for fluid transport as well as aesthetics. Here, the quilting pattern includes a 3-inch diamond pattern, but it should be understood that any number of patterns and designs may be utilized.

Figure 8:
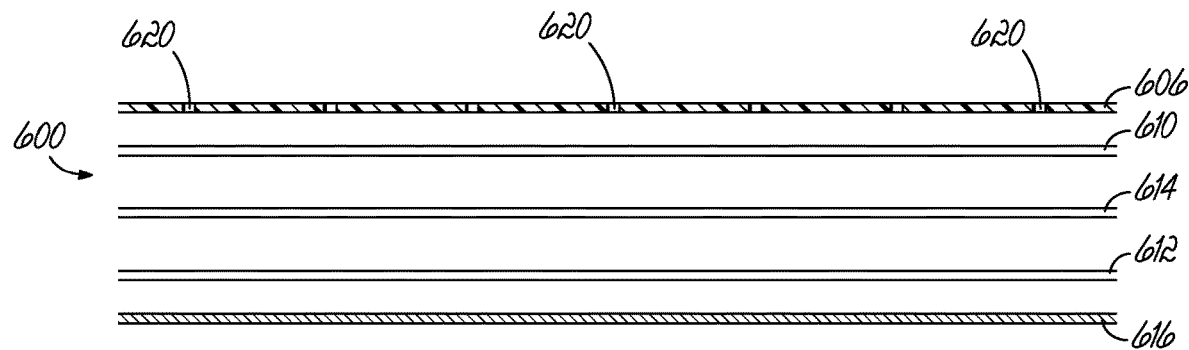
FIG. 8 is a cross-sectional view of a reusable incontinence pad in accordance with another embodiment of the invention.
Figure 9:
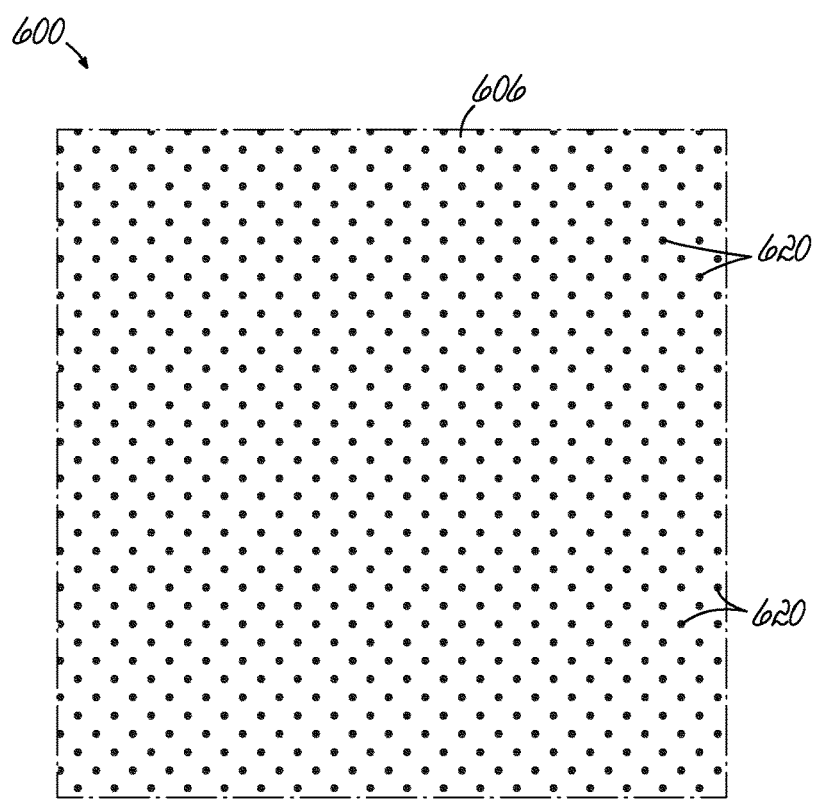
FIG. 9 is a top view of the reusable incontinence pad of FIG. 8 in accordance with an embodiment of the invention.

With reference now to FIG. 8, a cross-section of a reusable incontinence pad 600 in accordance with another embodiment of the invention is shown, which is a variation of the reusable incontinence pad of FIG. 6, with the exception that the quilting yarn is optionally omitted and openings, which here are circular holes 620, are formed in the top layer 606 to permit liquid(s), such as bodily fluids, to pass through the top plastic film and into the interior or middle layers, i.e., wicking layers 610, 612 and intermediate absorbent layer 614, which are as described above. The incontinence pad 600 further includes an outermost barrier layer 616. The openings (e.g., holes 620, slits, and the like) may be formed in the top layer 606 by means and methods known in the art (e.g., cut, punched, and the like). The sizes and shapes of the openings as well as the spacing and frequency of the openings therebetween can vary, as desired/needed, to control fluid flow. In one example, the openings can be round or circular in nature, be from about 1.5 mm to about 6.0 mm in size, and may be evenly spaced along the surface (e.g., along the length and/or width) of the film. In another example, the openings can be oval or elliptical in shape and be from about 1.5 mm×2.0 mm to 5.0 mm×7.0 mm in size, and may be evenly spaced along the surface (e.g., along the length and/or width) of the film. In one example, the oval size is 2.2 mm×1.5 mm. In another example, the openings can be slits cut into the film at various or regular intervals. The openings (e.g., holes 620), as shown in FIG. 9, may be arranged in a desired pattern in the incontinence pad 600 for fluid transport as well as aesthetic purposes. It should be understood that any number of patterns and designs may be utilized.

Again, ordinarily, if moisture or liquid were to be present on the user-side surface of the top layer 606, the moisture would not permeate through due, in large part, to the cohesive forces of the liquid(s) being unable to penetrate the top layer 606 and the lack of capillary presence or action of the plastic film. However, at least due to the presence of openings (e.g., holes or slits) in the film and a corresponding wicking layer(s) 610 and/or 612, which are as discussed above in the incontinence pad of FIG. 6, coming in contact with the top layer 606, particularly when a user is positioned on the incontinence pad 600, moisture or liquid is able to wick through by capillary forces, as explained above. In another embodiment, additional openings may be created in layers by quilting using an optional quilting yarn (not shown) to assist in the capillary transport or wicking action of the wicking layer(s) below the top layer 606.

In another embodiment of the invention, the top layer 106, 206, 306, 406, 506, 606 of each reusable incontinence pad 100, 100a, 200, 300, 400, 400a, 500, 600 can be a fabric substrate of a multifilament yarn that can include a chemical treatment to provide a desired hydrophobicity for the top layer. The chemically treated, multifilament fabric top layer both can provide a desirable hand or feel for the user and can help prevent moisture from permeating therethrough. In one example, the top layer 106, 206, 306, 406, 506, 606 is a multifilament polyester yarn and has a polyester warp knit construction, which has been chemically treated so as to provide a desired hydrophobicity. The top layer can be secured as part of the composite sheet as discussed above, such as via quilting or other securement means, for example.

Figure 10:
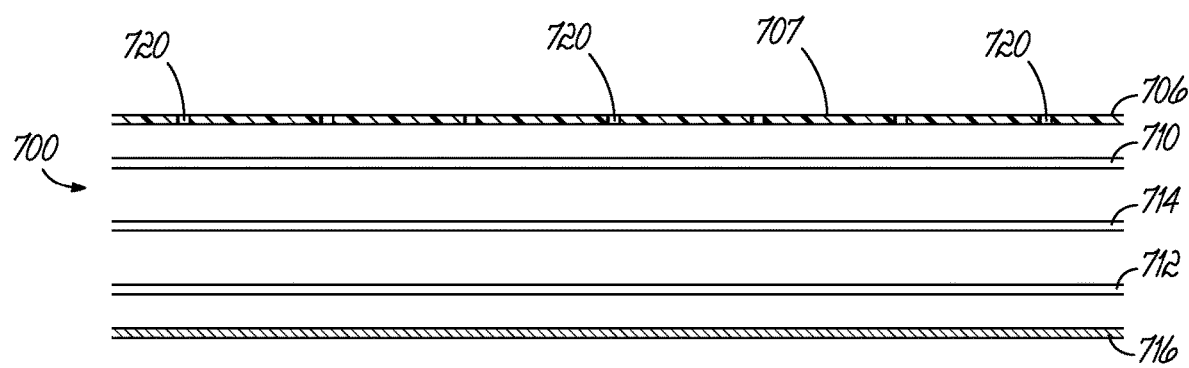
FIG. 10 is a cross-sectional view of a reusable incontinence pad in accordance with another embodiment of the invention.

With specific reference now to FIG. 10, a cross-section of a reusable incontinence pad 700 in accordance with an embodiment of the invention is shown, which is a variation of the reusable incontinence pad of FIG. 8 with the exception that the top layer 706 is a fabric substrate of a multifilament yarn that includes a chemical treatment 707 having a desired chemical treatment composition to provide a desired hydrophobicity that can help prevent moisture/liquid from permeating therethrough. In addition, the circular holes 620 of FIG. 8 have been replaced by oval-shaped holes that are formed in the top layer 706 to permit liquid(s), such as bodily fluids, to pass therethrough and into the interior or middle layers, i.e., wicking layers 710, 712 and intermediate absorbent layer 714, which are as described above, such as during an insult. The incontinence pad 700 further includes an outermost barrier layer 716.

Figure 11:
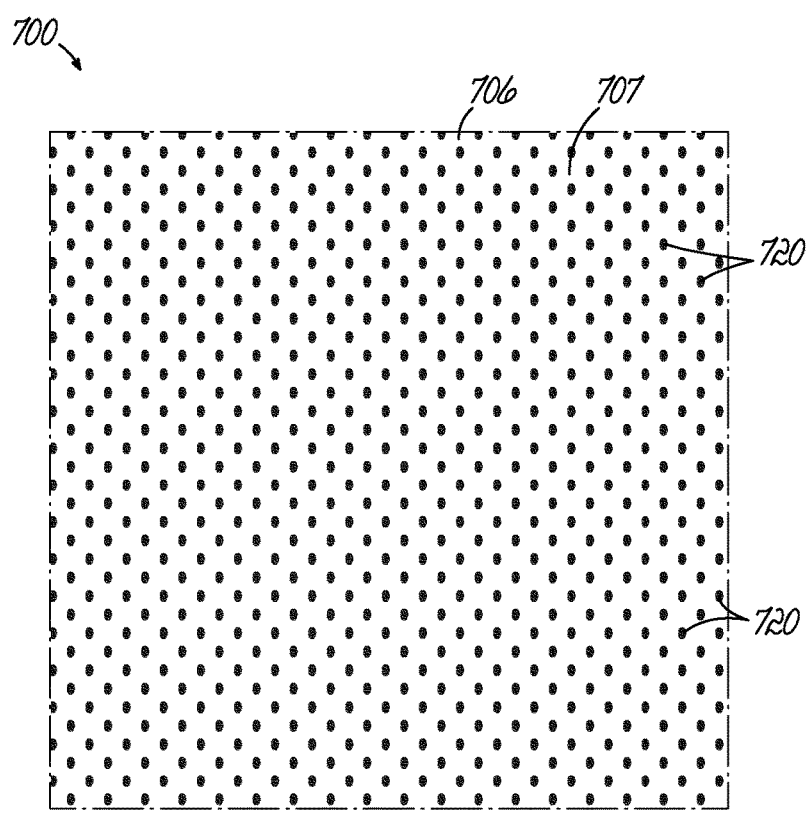
FIG. 11 is a top view of the reusable incontinence pad of FIG. 10 in accordance with an embodiment of the invention.

The openings 720 (e.g., ovals) may be formed therein by means and methods known in the art (e.g., cut, punched, formed during fabric formation, and the like). The sizes and shapes of the openings 720 as well as the spacing and frequency of the openings therebetween can vary, as desired/needed, to control fluid flow. In one example, the top layer 706 includes 15 to 30 openings 720 per square inch. In another example, the top layer 706 includes 20 to 25 openings 760 per square inch or, in another example, 21 to 24 openings per square inch. In one example, the openings 720 can be oval or elliptical in shape and be from about 2.0 mm×1.0 mm to 7.0 mm×5.0 mm in size, and may be evenly spaced along the surface (e.g., along the length and/or width) of the top layer 706. In another example, the oval size is 2.2 mm×1.5 mm. In still another example, the oval size is greater than 2.0 mm×1.0 mm or greater than 2.2 mm×greater than 1.5 mm. The oval openings 720, as shown in FIG. 11, may be arranged in a desired pattern in the incontinence pad 700 for fluid transport as well as aesthetic purposes. It should be understood that any number of patterns and designs may be utilized.

In accordance with another embodiment of the invention and with reference now to FIG. 12, a cross-section of a reusable incontinence pad 800 is shown, which is a variation of the reusable incontinence pad 100a of FIG. 2A, with the exception that barrier layer 816 defines a multilayer laminate composite, which is further described below, and the top layer 106 of FIG. 2A is replaced with a top layer 806 as just described above in FIGS. 10 and 11 (top layer 706). In particular, top layer 806 is a fabric substrate of a multifilament yarn that includes a chemical treatment 807 having a desired chemical treatment composition to provide a desired hydrophobicity that can help prevent moisture/liquid from permeating therethrough. In addition, the top layer 806 includes oval-shaped holes that are formed in the top layer 806 to permit liquid(s), such as bodily fluids, to pass therethrough and into the interior or middle layers, i.e., wicking layers 810 and 812, which are as described in FIG. 2A (wicking layers 210 and 212), such as during an insult. As discussed above, the openings 820 (e.g., ovals) may be formed therein by means and methods known in the art (e.g., cut, punched, formed during fabric formation, and the like). The sizes and shapes of the openings 720 as well as the spacing and frequency of the openings therebetween can vary, as desired/needed, to control fluid flow and are as discussed above with respect to FIGS. 10 and 11.

Figure 12:
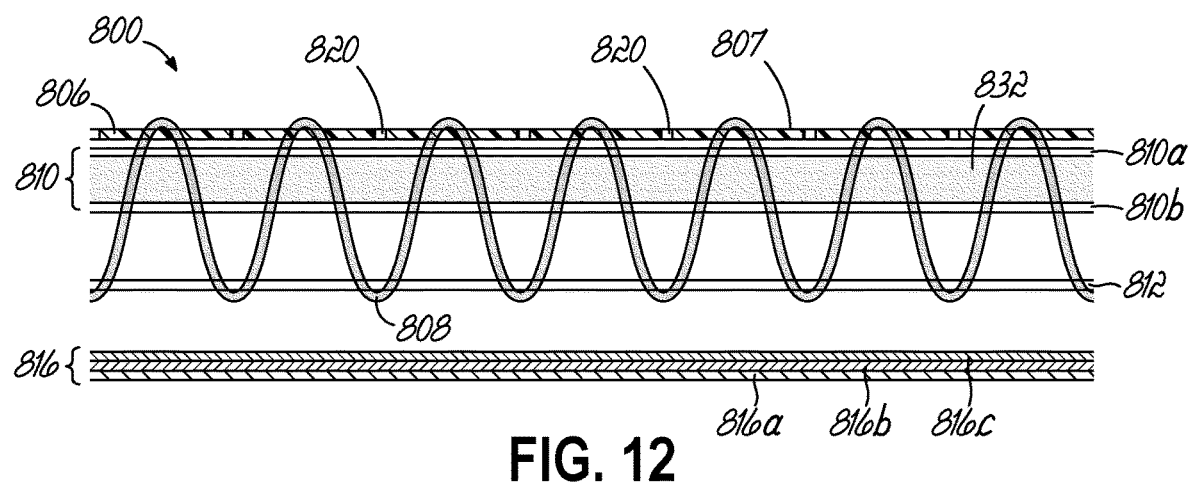
FIG. 12 is a cross-sectional view of a reusable incontinence pad in accordance with another embodiment of the invention.

With continuing reference to FIG. 12, the wicking layer 812 can include a woven and/or knitted layer of material that can come into contact with the wicking layer 810 and, more specifically, wicking layer 810b, and be configured to promote wicking of moisture from the wicking layer 810 therein. For example, the wicking layer 812 can be a knit layer that can include one or more different types of hydrophobic yarns, such as nylon, polyester, and the like. In one embodiment, the wicking layer 812 can include one or more plies of multifilament material. Filaments included in each of the plies of the wicking layer 812 may be the same material or different materials within the plies as well as among the plies. The wicking layer 812 can be composed of yarns having from 20 denier to 500 denier. In another example, the yarns can have from 20 denier to 400 denier. In another example, the wicking layer 812 can be composed of yarns having from 20 denier to 300 denier. In another example, the yarns can have from 50 denier to 300 denier. The wicking layer 812 can have a capillary size or dpf from about 0.3 to 5. In another example, the wicking layer 812 can have a capillary size or dpf from about 1 to 5. In another example, the wicking layer 812 can have a capillary size or dpf from about 1 to 4, about 1 to 3, or about 1 to 2. In another example, the wicking layer 812 can have a dpf of less than 1 or greater than 5. In one embodiment, the wicking layer 812 can be composed of 1-ply, 150 denier, and 34 filaments polyester having a 4.4 dpf.

With continued reference to FIG. 12, the wicking layer 810 with its wicking layers 810a, 810b, and layer of tuck yarns 832 can include only a single type of knit yarn in each layer 810a, 810b, 832 that provides for a clearly defined and increasing capillary gradient therein. More specifically, wicking layer 810a, 810b, and the layer of tuck yarns 832 can be a knit layer that can include one type of hydrophobic yarn, such as nylon, polyester, and the like. In one example, wicking layer 810a, 810b, and the layer of tuck yarns 832 can include one or more plies of multifilament material. The wicking layer 810a, 810b, and the layer of tuck yarns 832 can be composed of yarns having from 20 denier to 500 denier. In another example, the yarns can have from 20 denier to 400 denier. In another example, the yarns can have from 50 denier to 300 denier. In another example, the yarns can have from 50 denier to 150 denier. The wicking layer 810a, 810b, and the layer of tuck yarns 832 can have a capillary size or dpf from about 0.3 to 5. In another example, the wicking layer 810a, 810b, and the layer of tuck yarns 832 can have a capillary size or dpf from about 1 to 5. In another example, the wicking layer 810a, 810b, and the layer of tuck yarns 832 can have a capillary size or dpf from about 1 to 4, or about 1 to 3, or about 1 to 2. In another example, the wicking layer 810a, 810b, and the layer of tuck yarns 832 can have a dpf of less than 1 or greater than 5. In one specific embodiment, the wicking layer 810a can be composed of 1 ply, 75 denier, and 72 filament polyester having a 1.04 dpf, the tuck yarns 832 can be composed of a 1-ply, 100 denier, and 36 filament polyester with a 2.8 dpf, and the wicking layer 810b can be composed of a 2-ply, 150 denier, 34 filament polyester having 4.4 dpf.

The quilting yarn 808 is a yarn that connects the top layer 806 to the wicking layers 810, 812 via quilting means and methods known in the art. The quilting yarn 808 may be any suitable natural or synthetic yarn. In one example, the yarn 808 is a hydrophobic yarn, such as polyester, nylon, and the like. In one embodiment, the yarn is 100% polyester spun yarn. The yarn may be chemically treated to enhance the wicking of moisture. The quilting yarn 808 may be arranged in a quilting pattern in the incontinence pad 100.

The barrier layer 816, in this embodiment, can define a multilayer laminate composite. In this example, the barrier layer includes three layers 816a, 816b, and 816c, but can include more or less, as needed/desired. As shown in FIG. 12, the barrier layer 816 includes an outer scrim layer 816a, an intermediate film layer 816b, and an optional inner woven and/or knitted layer 816c, such as a polyester (e.g., 100% polyester) knit layer. The barrier layer 816 (and variations thereof) may be utilized in any of the prior embodiments for the reusable incontinence pad 100, 100a, 200, 300, 400, 400a, 500, 600, 700 as described above.

Concerning the outer scrim layer 816a, this layer can be a woven or knit layer that can include one or more different types of hydrophobic yarns, such as nylon, polyester, and the like, which can add strength and provide stability to the barrier layer 816 (and the incontinence pad 800 overall). In one example, the outer scrim layer 816a is a polyester scrim layer (e.g., a woven (mesh) polyester scrim layer). In another example, the scrim layer 816a can be a knit fabric, such as a polyester knit fabric.

The intermediate film layer 816b can include a laminated polyester film or other, impermeable (waterproof) material, such as a polyvinyl chloride (PVC), polyurethane, and the like.

As indicated above, the inner layer 816c is optional and can include a woven and/or knitted layer of material, which can come into contact with the wicking layer 112. In one example, the inner layer 816c can be a knit layer that can include one or more different types of hydrophobic yarns, such as nylon, polyester, and the like. In another example, the inner layer 816c can include one or more plies of multifilament material. Filaments included in each of the plies of the inner layer 816c may be the same material or different materials within the plies as well as among the plies. The inner layer 816c can be composed of yarns having from 20 denier to 500 denier. In another example, the yarns can have from 20 denier to 400 denier. In another example, the inner layer 816c can be composed of yarns having from 20 denier to 300 denier. In another example, the yarns can have from 50 denier to 300 denier. The inner layer 816*c* can have a capillary size or dpf from about 0.3 to 5. In another example, the inner layer 816*c* can have a capillary size or dpf from about 1 to 5. In another example, the inner layer 816*c* can have a capillary size or dpf from about 1 to 4, about 1 to 3, or about 1 to 2. In another example, the inner layer 816*c* can have a dpf of less than 1 or greater than 5. In one embodiment, the inner layer 816*c* can be composed of 1-ply, 150 denier, and 34 filaments polyester having a 4.4 dpf. In one example, the inner layer 816*c* can be an inner knit layer or an inner warp knit layer, such as a warp polyester knit layer. In another example, the inner layer 816*c* is a woven layer, such as a polyester woven layer.

The barrier layer 816, with its multilayer laminate composite, can be formed by means and methods known in the art, such as by heat pressing together the layers to form an assembled barrier layer 816. Cutting/sizing of the barrier layer 816 or individual layers 816*a*, 816*b*, 816*c* can be performed before or after lamination.

Concerning the transport and capture of liquid from the top layer 706, 806 to the interior of the incontinence pad 700, 800, ordinarily, if moisture or liquid were to be present on the user-side surface of the top layer 706, 806, the moisture would not permeate through due, in large part, to the cohesive forces of the liquid(s) being unable to penetrate the chemically treated top layer 706, 806 and the lack of capillary presence or action thereof. However, at least due to the presence of openings 720, 820 (e.g., ovals) in the top layer 706, 806 and a corresponding wicking layer(s) 710, 810 coming in contact with the top layer 706, 806, particularly when a user is positioned on the incontinence pad 700, 800, moisture or liquid is able to wick through by capillary forces, which is discussed in greater detail below. In another embodiment, additional openings may be created in the various layers of the incontinence pad 700, 800 by quilting using a quilting yarn 808 (not shown in FIG. 10) to assist in the capillary transport or wicking action of the wicking layer(s) below the top layer 706, 806.

Concerning the capillary action and wicking of moisture/liquid in the various embodiments, particularly those with openings 620, 720, 820, a cylindrical column of water can move upward through a capillary, which can be defined, in part, by the openings 620, 720, 820 in the top layer 606, 706, 806 via cohesive forces to the sidewalls of the capillary overcoming opposing gravitational forces. This upward force is referred to as capillary action. With specific reference to FIGS. 10-12, the pores or openings 720, 820 of the top layer 706, 806 can be considered inverse capillary openings. When the top layer 706, 806 is imbued with anti-rewetting properties, via the chemical treatment 707, 807, the openings 720, 820 can resist downward gravitational forces in a manner inversely proportional to natural capillary action. The desirable circumference of the openings 720, 820 may be determined experimentally using a water droplet of known volume with a specific surface energy. When the opening circumference is below a desired value, the observable phenomenon can be a near spherical water droplet remaining intact and stably balanced on top of the top layer 706, 806. Above this desirable circumference, the capillary opening of the opening 720, 820 can no longer oppose the gravitational forces of the cylindrical water column within a water droplet of a height h and the water droplet can pass, e.g., rapidly pass, through the top layer 706, 806 into the layers below. Any (biological) liquid insult, for example, that contains a water column greater than this height h can also pass through the openings 720, 820 of the top layer 706, 806. This net downward flow of liquid creates a low-pressure zone across the opening 720, 820 that pulls the full liquid volume through the top layer 706, 806, such as by way of a continuous stream. Once this full liquid volume is below the top layer 706, 806, it is desirable that the anti-rewetting properties of the top layer 706, 806 does not wick the liquid back to the obverse face of the top layer 706, 806. The anti-rewetting properties of the top layer 706, 806, due to its chemical treatment, reduce the adhesive forces of the edges of the openings 720, 820 to near zero, thereby preventing/helping to prevent the capillary rise of liquid back to the face of the top layer 706, 806. This initial adhesion of the liquid to the edges of the openings 720, 820 would be a first step of the capillary process that brings liquid back to the surface. However, the anti-rewetting features, which includes the chemical treatment 707, 807, of the top layer 706, 806 disrupts this process.

Concerning the top layer 706, 806, the top layer 706, 806, with its fabric substrate of a multifilament yarn, may be formed from fibers such as synthetic fibers, natural fibers, or man-made fiber using natural constituents or combinations thereof. Synthetic fibers can include, for example and without limitation, polyester, acrylic, polyamide, polyolefin, polyaramid, polyurethane, regenerated cellulose, and blends thereof. Polyester can include, for example, polyethylene terephthalate, polytriphenylene terephthalate, polybutylene terephthalate, polylactic acid, and combinations thereof. Polyamide can include, for example, nylon 6, nylon 6,6, and combinations thereof. Polyolefin can include, for example, polypropylene, polyethylene, and combinations thereof. Polyaramid can include, for example, poly-p-phenyleneteraphthalamid (e.g., Kevlar®), poly-m-phenyleneteraphthalamid (e.g., Nomex®), and combinations thereof. Natural fibers can include, for example and without limitation, wool, cotton, linen, ramie, jute, flax, silk, hemp, or blends thereof. Exemplary man-made materials using natural constituents can include regenerated cellulose (e.g., rayon), lyocell, or blends thereof. The textile substrate may be formed from fibers or yarns of any size, including microdenier fibers and yarns (fibers or yarns having less than one denier per filament). The fibers or yarns also may include spun fibers, continuous filament fibers, bicomponent fibers, bicomponent splittable fibers, or blends thereof. The fibers also may include slit film fibers or tape yarn. In one example, the top layer 706, 806 has a knit construction (e.g., a polyester (warp) knit construction).

In one example, the weight of the top layer 706, 806 can be from about 40 gsm to 150 gsm. In another example, the weight of the top layer 706, 806 can be from about 70 gsm to about 150 gsm. In another example, the weight of the top layer 706, 806 can be from about 80 gsm to about 130 gsm. In still another example, the weight of the top layer 706, 806 can be from about 95 gsm to about 120 gsm. In another example, the weight of the top layer 706, 806 can be from 100 gsm to 110 gsm. In another example, the weight of the top layer 706, 806 can be less than 100 gsm (e.g., 73 gsm).

As indicated above, the chemical treatment 707, 807 of the top layer 706, 806 is not intended to completely limit absorption of moisture during transport from the source to a layer or layers within the incontinence pad 700, 800, such as a wicking layer(s) 710, 810, 712, 812 and the intermediate absorbent layer 714, for example, but to limit moisture/liquid absorption within or throughout the yarns of the top layer 706, 806. This can be achieved by applying a specified amount of a desired chemical treatment composition to the top layer 706, 806 by means and methods known in the art, as discussed above. In one example, the chemical treatment composition defines a hydrophobic chemical composition or a chemical composition with hydrophobic imparting properties to at least the top layer 706, 806. The chemical treatment composition can include one or more moisture or liquid repellent compounds, a hydrophobic crosslinker (or binder) system(s), or combinations thereof. With the use of a repellant (or hydrophobic) compound(s) or chemical composition(s) with hydrophobic imparting properties, these approaches can minimize absorption through repellency in the top layer 706, 806, for example whereby the top layer 706, 806 behaves like hydrophobic monofilament and, thus, prevents or limits absorption and transport of liquid(s) through the yarns of the top layer 706, 806. Repellent compounds and/or cross-linkers/binders also can be used to improve other aspects of the top layer 706, 806, such as hand, comfort, co-efficient of friction, and the like. The cross-linking chemistry also can be used to improve the laundry durability of the repellent chemistry.

Suitable examples of the moisture/liquid repellant compounds can include fluorochemicals, such as polytetrafluoroethylene (PTFE), perfluorobutanesulfonic acid (PFBS), fluorinated urethane, perfluoroalkyl-ethylacrylate-based fluororesin emulsions, fluoroalkyl acrylate copolymers, combinations thereof, and the like. Exemplary commercial products can include the Scotchgard family of repellent fluorochemicals by 3M, the Zonyl family of repellent fluorochemicals by Dupont, the Repearl® family of repellent fluorochemicals by Mitsubishi International Corporation, and the Unidyne family of repellant fluorochemicals by Daikin (e.g., Unidyne TG56-01). In addition to fluorochemicals, other repellent chemicals, such as silicones, waxes, acrylic polymers, and the like, may also be used to achieve repellent properties for the top layer 706 806. Suitable silicones include amino functionalized silicones, such as amino-functional silicone emulsions (e.g., microemulsion). Exemplary commercial products of the repellent silicones include Ultratex SI available from Huntsman.

Suitable examples of the cross-linking/binding system(s) can include hydrophobic cross-linkers such as protected diisocyanates and protected isocyanates or protected derivatives of isocyanates and the like, or combinations thereof. Other suitable examples include monomers or polymers containing two or more blocked isocyanate compounds, polyurethanes, acrylonitrile acrylic copolymers, such as acrylonitrile acrylic copolymer emulsion binder, stearylated melamine methylol resins, long-chain fatty acrylate copolymer emulsions, combinations thereof, and the like. Exemplary commercial products can include Repearl® MF™ available from Mitsubishi Corp, Arkophob® (a polyurethane) or Arkophob DAN, which is a hydrophobic cross-linking component that is a protected isocyanate, available from Clariant, Hydrophobol® Xan™ available from DuPont, Synthebond™ available from Synthomer, which is an acrylonitrile acrylic copolymer emulsion binder, Sequapel™ available from Synthomer, which is a stearylated melamine methylol resin, and Smartrepel® available from Archroma, which is a long-chain fatty acrylate copolymer emulsion. In one example, the cross-linking/binding system is fluorine free.

As indicated above, in one example, the chemical treatment composition can include a mixture of a fluoroalkyl acrylate copolymer, a protected isocyanate, and an amino functionalized silicone. In another example, the chemical treatment composition can include a mixture of a fluoroalkyl acrylate copolymer and a protected isocyanate or a protected isocyanate and an amino functionalized silicone. In another example, the chemical treatment composition can include a mixture of an acrylonitrile acrylic copolymer emulsion binder and a protected isocyanate. Still yet, in another example, the chemical treatment composition can include a mixture of a stearylated melamine methylol resin, an acrylonitrile acrylic copolymer emulsion binder, and a protected isocyanate.

In the chemical treatment composition, the total weight of the one or more moisture or liquid repellent compounds, the hydrophobic crosslinker or binder system(s), or combinations thereof can include 0.1% to 5% by weight of the chemical treatment composition, with the remainder, for example, being an aqueous liquid, such as water and the like. In another example, the total weight of the one or more moisture or liquid repellent compounds, the hydrophobic crosslinker or binder system(s), or combinations thereof can include 1% to 4% or 2% to 4% by weight of the chemical treatment composition, and the remainder can be an aqueous liquid, such as water and the like. In still another example, the total weight of the one or more moisture or liquid repellent compounds, the hydrophobic crosslinker or binder system(s), or combinations thereof can include about 3.4% by weight of the chemical treatment composition, and the remainder can be an aqueous liquid, such as water and the like.

Representative commercial products, which can include an active component defining a moisture or liquid repellent compound or a hydrophobic crosslinker/binder system, and the corresponding amounts of that commercial product for providing an exemplary chemical treatment composition herein can include the following:

| Chemical Treatment composition | Commercial Products | % (rest is water) |
|---|---|---|
| 1 | [1]Unidyne TG5601 | 5% |
| | [2]Arkophob DAN | 2% |
| | [3]Ultratex SI | 1% |
| 2 | Unidyne TG5601 | 2% |
| | Arkophob DAN | 2% |
| 3 | Arkophob DAN | 2% |
| 4 | Unidyne TG5601 | 1% |
| | Arkophob DAN | 2% |
| | Ultratex SI | 1% |
| 5 | Unidyne TG5601 | 0.5% |
| | Arkophob DAN | 2% |
| | Ultratex SI | 1% |
| 6 | Unidyne TG5601 | 0.2% |
| | Arkophob DAN | 2% |
| | Ultratex SI | 1% |
| 7 | Unidyne TG5601 | 0.2% |
| | Arkophob DAN | 2% |
| 8 | Unidyne TG5601 | 2% |
| | Arkophob DAN | 3% |
| | Ultratex SI | 2% |
| 9 | Ultratex SI | 5% |
| | Arkophob DAN | 3% |
| 10 | [4]Synthebond XA-2437 | 5% |
| | Arkophob DAN | 2% |
| 11 | [5]Sequapel 409 | 5% |
| | Synthebond XA-2437 | 5% |
| | Arkophob DAN | 2% |

[1]available from Daikin, a fluoroalkyl acrylate copolymer
[2]available from Clariant, a protected isocyanate
[3]available from Huntsman, an amino functionalized silicone
[4]available from Synthomer, an acrylonitrile acrylic copolymer emulsion binder
[5]available from Synthomer, a stearylated melamine methylol resin Application of the chemical treatment composition to the top layer 706, 806, such as the outer/user surface thereof or the entirety of the top layer 706, 806, may be accomplished by means and methods known in the art, which can include, but are not limited to, coating, padding, spraying, foam coating, knife coating, printing, exhaustion techniques or by any other technique whereby one can apply an amount, for example, a controlled amount of a liquid suspension of the chemical treatment composition to the textile substrate, e.g. the top layer 706, 806. Employing one or more of these application techniques can allow the chemical treatment composition to be applied to the top layer 706, 806 in a desired (e.g., uniform) manner so that the top layer 706, 806 is sufficiently coated/treated. In one example, a length of the top layer fabric, e.g., a 120 gsm polyester warp knit fabric, with about 21-24 pores/sq. inch and a pore dimension of 2.36 mm×1.03 mm, can be impregnated with the desired chemical treatment composition by way of padding, as is known in the art, which can result in a wet pick-up of about 60-80% by weight of the fabric. The fabric then can be dried and cured for an acceptable amount of time (e.g., about 4 minutes) in an oven, such as a convection oven, at a suitable temperature (e.g., about 191° C. (390° F.)).

Generally speaking, conventional techniques/means and methods known in the art may be employed to make the various embodiments of the reusable incontinence pad 100, 100a, 200, 300, 400, 400a, 500, 600, 700, 800 of the present invention. In one example, the various layers (e.g., 806, 810, and 812) can be separately prepared, where each layer initially can be appropriately sized, e.g., cut to a desired size, then the layers (excluding the barrier) can be layered accordingly, followed by sewing or stitching together, and then optionally quilting 808 the stitched or sewn layers. The top layer 706, 806, in desired embodiments, may be separately chemically treated 707, 807 with a chemical treatment composition, such as by subjecting the top layer 706, 806 to a desired treatment process, e.g., padding, prior to sizing and/or layering, for example. As indicated above, the barrier layer (e.g., 816) can be separately prepared, such as by being appropriately sized, e.g., cut to a desired size, with lamination of multilayers of the barrier layer occurring as needed. The barrier layer then can be layered with the already sewn/stitched other layers and all layers sewn or stitched together. It should be appreciated by those of ordinary skill in the art that the various steps above may be rearranged or modified, as needed/desired. In one example, the layers may be sized after sewing or stitching, or quilting may occur prior to cutting, and the like.

Various incontinence pad samples with top layers chemically treated, as set out in Table 1 below, were constructed in accordance with the description of the incontinence pad 800 of FIG. 12 and absorption and rewet tested with top layers having different sized oval openings (constant size throughout the top layer of the pad), different numbers of oval openings per square inch, and different weights. The same chemical treatment composition was used on each top layer, as noted in Table 1. Here, the top layer fabric was impregnated with the chemical treatment composition by way of padding, as is known in the art. The fabric was dried and cured for about 4 minutes in a convection oven at about 191° C. (390° F.). For each sample, each of the top layers included a fabric substrate of a multifilament polyester having a warp knit construction. The incontinence pad samples also had two wicking layers, like wicking layers 810 and 812, along with a barrier layer, like barrier layer 816, as discussed above in FIG. 12. Specifically, for the samples, the wicking layers 810a, 810b and tuck yarns 832 therebetween included multifilament knit layers composed of polyester (1 ply, 75 denier, and 72 filament 1.04 dpf (810a), followed by 1 ply, 100 denier, 36 filament (tuck yarns), followed by 2 ply, 150 denier, 34 filaments @ 4.4 dpf (810b)), the wicking layer 812 included a multifilament polyester knit (1 ply, 150 denier, and 34 filaments @ 4.4 dpf), and the barrier layer defined a multilayer laminate composite including an outer polyester scrim, an intermediate laminated polyurethane film, and an inner 100% polyester knit.

To determine absorption and rewetting properties, each pad was subjected to an insult defined by 50 ml of water that was poured on to the outer surface of the top layer of the various incontinence pad samples. Absorption was measured in seconds and involved the time required to absorb all the liquid after an insult, as visually observed. Although essentially instant absorption was considered to be ideal, an absorption time of 30 sec or less was desirable. And rewet was measured by using blotting paper with 1 kg weight 2 min after the insult. With the rewetting test, any liquid from the underlying layers of the incontinence pad may come back to the user side of the top layer and wet the blotting paper making it heavier. The % rewet=(Final weight of blotting paper—Initial weight of blotting paper)/Initial weight of blotting paper. A lower % rewet indicates better performance as compared to a higher % rewet, with "0" indicating no rewetting.

TABLE 1

| Sample | Weight of top layer gsm | Top layer composition | Chemical Treatment Padding Formulation | Curing | Opening size mm × mm | Ovals/sq. inch | Absorption time (50 ml) sec | Rewet % |
|---|---|---|---|---|---|---|---|---|
| 1 | 110 | Polyester | 5% Unidyne | 390° F. | 1.2 × 0.8 | >24 | 90 | 0% |
| 2 | 110 | Polyester | TG5601[1] | @ 4 min | 1.38 × 1.04 | >24 | 60 | 0% |
| 3 | 138 | Polyester | 3% Arkophob | | 2.18 × 1.1 | 21 | 25 | 0% |
| 4 | 132 | Polyester | DAN[2] | | 2.2 × 1.2 | 21 | 20 | 0% |
| 5 | 120 | Polyester | 2% Ultratex SI[3] | | 2.36 × 1.03 | 24 | 20 | 0% |
| 6 | 115 | 68D Poly | (remainder | | 2.62 × 1.18 | 21 | 20 | 0% |
| 7 | 100 | Polyester | water) | | 2.64 × 1.22 | 21 | 30 | 0% |
| 8 | 71 | Polyester | | | 3.14 × 1.69 | 15 | <5 | 0% |
| 9 | 80 | Polyester | | | 3.14 × 2.2 | 21 | <5 | 0% |
| 10 | 110 | 75 D Poly | | | 4.07 × 1.35 | 12 | 20 | 0% |

[1]available from Daikin, a fluoroalkyl acrylate copolymer.
[2]available from Clariant, a protected isocyanate.
[3]available from Huntsman, an amino functionalized silicone.

From the above test data in Table 1, it was determined that the top layers having a weight less than 100 gsm, oval openings sized greater than 2.2 mm×greater than 1.5 mm, and less than 24 oval openings per square inch provided the most desirable absorption properties when treated chemically with a hydrophobic chemical treatment.

To further evaluate the durability/reusability of the incontinence pads in accordance with embodiments of the present invention, various samples of a selected incontinence pad with different chemical treatment compositions applied thereon were subjected to an industrial laundry process through 50 cycles with drying times being about 45 minutes using a temperature of about 160° F. Rewet data was obtained on each incontinence pad sample after laundering 1×, 5×, 10×, 25×, and 50×.

The incontinence pad samples, as set out in Table 2 below, included about 21-24 ovals per sq. inch and oval openings that were 2.36 mm×1.03 mm in dimension. Here, the top layer fabric was impregnated with the noted chemical treatment composition by way of padding, as is known in the art. The padded fabric then was dried and cured for about 4 minutes in a convection oven at about 191° C. (390° F.). Each of the top layers included a fabric substrate of a multifilament polyester having a warp knit construction and weighing about 120 gsm. The incontinence pad samples also had two wicking layers, like wicking layers 810 and 812, along with a barrier layer, like barrier layer 816, as discussed above in FIG. 12. Specifically, for the samples, the wicking layers 810a, 810b and tuck yarns 832 therebetween included multifilament knit layers composed of polyester (1 ply, 75 denier, and 72 filament 1.04 dpf (810a), followed by 1 ply, 100 denier, 36 filament (tuck yarns), followed by 2 ply, 150 denier, 34 filaments @ 4.4 dpf (810b)), the wicking layer 812 included a multifilament polyester knit (1 ply, 150 denier, and 34 filaments @ 4.4 dpf), and the barrier layer defined a multilayer laminate composite including an outer polyester scrim, an intermediate laminated polyurethane film, and an inner 100% polyester knit.

To determine the rewetting properties of the laundered incontinence pads and reusability thereof, each pad initially was subjected to an insult defined by 50 ml of water that was poured on to the outer surface of the top layer of the various incontinence pad samples. The "soiled" incontinence pads then were laundered, as noted above. And then the insult/soiling and laundering process was repeated. The rewet properties of each pad were measured after the first laundering, the fifth laundering, the tenth laundering, the twenty-fifth laundering, and the fiftieth laundering by using blotting paper with 1 kg weight 2 min after the insult. The rewet test results are noted below in Table 2 and discussed thereafter.

TABLE 2

| | | | Rewet Test | | | | |
|---|---|---|---|---|---|---|---|
| | | Curing | 1× | 5× | 10× | 25× | 50× |
| 1 | Control (treated with water) | 390° F./ 4 min | 152% | 156% | 116% | 164% | 183% |
| 2 | 5% Unidyne TG5601[1] 3% Arkophob DAN[2] 2% Ultratex SI[3] | | 5% | 5% | 3% | 2% | 3% |
| 3 | 2% Unidyne TG5601 3% Arkophob DAN 2% Ultratex SI | | 0% | 5% | 0% | 3% | 6% |
| 4 | 1% Unidyne TG5601 3% Arkophob DAN 2% Ultratex SI | | 3% | 2% | 3% | 5% | 3% |
| 5 | 0.5% Unidyne 5601 3% Arkophob DAN 2% Ultratex SI | | 0% | 5% | 5% | 5% | 3% |
| 6 | 5% Ultratex SI 3% Arkophob DAN | | 2% | 11% | 5% | 5% | 14% |
| 7 | 5% Ultratex SI 5% Arkophob DAN | | 5% | 14% | 3% | 5% | 5% |
| 8 | 10% Ultratex SI 5% Arkophob DAN | | 5% | 11% | 2% | 2% | 5% |
| 9 | 5% Smart Repel[4] 3% Akophob DAN 10% Ultratex SI | | 0% | 0% | 3% | 3% | 20% |
| 10 | 5% Smart Repel 3% Arkophob DAN 5% Synthebond XA-2437[5] 5% Ultratex SI | | 2% | 2% | 5% | 3% | 3% |
| 11 | 5% Sequapel[6] 3% Arkophob DAN 5% Synthebond XA-2437 5% Ultratex SI | | 5% | 2% | 5% | 3% | 3% |

[1]available from Daikin, a fluoroalkyl acrylate copolymer.
[2]available from Clariant, a protected isocyanate.
[3]available from Huntsman, an amino functionalized silicone.
[4]available from Archroma, a long-chain fatty acrylate copolymer emulsion.
[5]available from Synthomer, an acrylonitrile acrylic copolymer emulsion binder.
[6]available from Synthomer, a stearylated melamine methylol resin.

From the above rewet test data in Table 2, it was determined that the tested samples (and the like), aside from the control, produced (and would produce) the desired functionality. See e.g., chemical treatment compositions for Samples 2-11, which performed satisfactorily even after 50 insults and subsequent launderings, with the most desirable chemical treatment composition being those including a fluoroalkyl acrylate copolymer, an amino functionalized silicone, and combinations thereof. An important aspect concerning chemical treatment ultimately is preventing liquid from wicking into the various capillaries of the top layer but permitting passage through the openings therein to the underlaying wicking layer(s).

By virtue of the foregoing, there is thus provided an improved textile with moisture or liquid wicking and absorbing properties for use as a reusable incontinence pad 100, 100a, 200, 300, 400, 400a, 500, 600, 700 that is able to wick and retain moisture or liquid away from its user. The hydrophobic top layer of the incontinence pad ensures that moisture or liquid, such as bodily fluids (e.g., urine, blood, etc.) does not remain near the top layer, but is rather, wicked into and through the incontinence pad, driven by capillary forces. In the end, the incontinence pad can help protect the user from wetness and skin irritation and help prevent infection from bodily fluids, is durable enough to withstand repeated launderings, and also is comfortable to the user. While the above textile or reusable pad with moisture or liquid wicking and absorbing properties has been described in detail above with respect to use as a reusable incontinence pad, it should be understood that any number of other items and/or other applicable uses can be identified, such as panty liners, baby diapers, adult diapers or underwear, and wound care such as bandages/band aids, for example. In addition, even though the pad (e.g., incontinence pad) has been discussed hereinabove as being "reusable", the pads of the present invention may treated or used, if so/as desired, as a disposable pad and discarded after just one use, for example.

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. Thus, the invention in its broader aspects is therefore not limited to the specific details, representative apparatus and method and illustrative example shown and described. Accordingly, departures may be made from such details without departing from the spirit or scope of applicant's general inventive concept.

What is claimed is:

1. A reusable pad comprising:
   a fabric top layer having a user-side surface for being situated adjacent a user and including a multifilament yarn, the top layer having a plurality of spaced apart openings formed therethrough and having a chemical treatment composition applied thereto, the chemical treatment composition including one or more hydrophobic chemical compounds and/or one or more chemical compounds that impart hydrophobic properties to the top layer, wherein the chemical treatment composition provides a desired hydrophobicity to the top layer such that liquid from the user passes through the user-side surface of the top layer via only the spaced apart openings;
   a bottom barrier layer that includes an impermeable layer; and
   a first wicking layer situated between the top layer and the bottom barrier layer, the first wicking layer including a plurality of first wicking layer sub-layers including one or more plies of multifilament hydrophobic yarn with one sub-layer being adjacent the top layer and each of the plurality of sub-layers having a corresponding dpf (denier per filament) value wherein the dpf values for each sub-layer increases when moving in a direction away from the top layer to provide a capillary gradient that promotes migration of liquid from the user in a direction away from the top layer.

2. The reusable pad of claim 1 wherein the top layer includes a polyester multifilament yarn.

3. The reusable pad of claim 1 wherein the plurality of spaced apart openings are oval-shaped.

4. The reusable pad of claim 1 wherein the top layer has a length and a width and the plurality of spaced apart openings formed therethrough extend along the length and/or width of the top layer and wherein the spaced apart openings are evenly spaced.

5. The reusable pad of claim 1 wherein the top layer includes about 15 to 30 openings per square inch.

6. The reusable pad of claim 1 wherein the spaced apart openings are from about 2.0 mm×1.0 mm to 7.0 mm×5.0 mm in size.

7. The reusable pad of claim 1 wherein the top layer is a fabric having a weight ranging from about 40 gsm to about 150 gsm.

8. The reusable pad of claim 1 wherein the one or more hydrophobic chemical compounds include a fluorochemical, silicone, wax, acrylic polymer, or combinations thereof and the one or more chemical compounds that impart hydrophobic properties to the top layer include a protected diisocyanate, protected isocyanate, protected derivative of an isocyanate, a monomer or polymer containing two or more blocked isocyanate compounds, polyurethane, acrylonitrile acrylic copolymer, stearylated melamine methylol resin, long-chain fatty acrylate copolymer emulsion, or combinations thereof.

9. The reusable pad of claim 1 wherein the chemical treatment composition includes 0.1% to 5% by total weight of the one or more hydrophobic chemical compounds, the one or more chemical compounds that impart hydrophobic properties to the top layer, or combinations thereof by weight of the chemical treatment composition.

10. The reusable pad of claim 1 wherein the plurality of first wicking layer sub-layers includes (a) a first wicking sub-layer situated adjacent the top layer, (b) a sub-layer of tuck yarns, and (c) a second wicking sub-layer, the sub-layer of tuck yarns between and connecting the first and second wicking sub-layers, the first wicking sub-layer including one or more plies of multifilament hydrophobic yarn and having a first dpf value, the sub-layer of tuck yarns including one or more plies of multifilament hydrophobic yarn and having a second dpf value, and the second wicking sub-layer including one or more plies of multifilament hydrophobic yarn and having a third dpf value, wherein the first dpf value is smaller than the second dpf value with the second dpf value being smaller than the third dpf to provide the capillary gradient that promotes migration of liquid from the user in a direction away from the top layer towards the second wicking sub-layer.

11. The reusable pad of claim 1 wherein each of the plurality of first wicking layer sub-layers includes one or more plies of multifilament polyester yarn.

12. The reusable pad of claim 1 wherein the dpf values for each sub-layer are in a range from about 0.3 to about 5 dpf.

13. The reusable pad of claim 1 wherein each of the plurality of first wicking layer sub-layers is composed of multifilament hydrophobic yarn having from 20 denier to 500 denier.

14. The reusable pad of claim 1 wherein the barrier layer defines a multilayer laminate composite that includes an outer scrim layer, an intermediate impermeable film layer, and an optional inner woven and/or knitted layer.

15. The reusable pad of claim 1 further comprising a second wicking layer situated between the barrier layer and the first wicking layer, the second wicking layer including one or more plies of multifilament hydrophobic yarn.

16. The reusable pad of claim 1 wherein the fabric top layer and first wicking layer are quilted together.

17. The reusable pad of claim 1 wherein the reusable pad defines a reusable incontinence pad.

18. The reusable pad of claim 1 wherein the reusable pad is used in or as a panty liner or a diaper.

19. The reuseable pad of claim 1 wherein the reusable pad can be washed, dried, and reused at least multiple times.

20. A reusable pad comprising:
a fabric top layer having a user-side surface for being situated adjacent a user and including a polyester multifilament yarn that defines a polyester knit construction, the top layer having a plurality of spaced apart oval-shaped openings formed therethrough along a length and width of the top layer, the top layer includes about 15 to 30 oval-shaped openings per square inch with the oval-shaped openings being from about 2.0 mm×1.0 mm to 7.0 mm×5.0 mm in size, the top layer having a chemical treatment composition applied thereto, the chemical treatment composition including one or more hydrophobic chemical compounds and/or one or more chemical compounds that impart hydrophobic properties to the top layer, wherein the chemical treatment composition provides a desired hydrophobicity to the top layer such that liquid from the user passes through the user-side surface of the top layer via only the spaced apart openings;
a bottom barrier layer that defines a multilayer laminate composite, which includes an outer scrim layer, an intermediate impermeable film layer, and an optional inner woven and/or knitted layer;
a first wicking layer situated below and adjacent the top layer, the first wicking layer includes a first wicking sub-layer situated adjacent the top layer, a sub-layer of tuck yarns, and a second wicking sub-layer, the sub-layer of tuck yarns between and connecting the first and second wicking sub-layers, the first wicking sub-layer including one or more plies of multifilament hydrophobic yarn and having a first dpf (denier per filament) value, the sub-layer of tuck yarns including one or more plies of multifilament hydrophobic yarn and having a second dpf value, and the second wicking sub-layer including one or more plies of multifilament hydrophobic yarn and having a third dpf value, wherein the first dpf value is smaller than the second dpf value with the second dpf value being smaller than the third dpf to provide a capillary gradient that promotes migration of liquid from the user in a direction away from the top layer and towards the second wicking sub-layer; and
a second wicking layer situated between the barrier layer and the first wicking layer, the second wicking layer including one or more plies of multifilament hydrophobic yarn and having a dpf value greater than or equal to the first dpf value,
wherein the woven top layer, the first wicking layer, and the second wicking layer are quilted together via a hydrophobic yarn.

21. The reusable pad of claim 20 wherein the top layer is formed from a 100% polyester multifilament yarn that defines a polyester warp knit construction.

22. The reusable pad of claim 20 wherein the spaced apart openings are evenly spaced.

23. The reusable pad of claim 20 wherein the top layer includes about 20 to 25 oval-shaped openings per square inch.

24. The reusable pad of claim 20 wherein the top layer is a fabric having a weight ranging from about 40 gsm to about 150 gsm.

25. The reusable pad of claim 20 wherein the one or more hydrophobic chemical compounds include a fluorochemical, silicone, wax, acrylic polymer, or combinations thereof and the one or more chemical compounds that impart hydrophobic properties to the top layer include a protected diisocyanate, protected isocyanate, protected derivative of an isocyanate, a monomer or polymer containing two or more blocked isocyanate compounds, polyurethane, acrylonitrile acrylic copolymer, stearylated melamine methylol resin, long-chain fatty acrylate copolymer emulsion, or combinations thereof.

26. The reusable pad of claim 25 wherein the one or more chemical compounds that impart hydrophobic properties to the top layer are fluorine free.

27. The reusable pad of claim 20 wherein the chemical treatment composition includes a combination of a fluorochemical, a silicone, and a protected isocyanate.

28. The reusable pad of claim 20 wherein the chemical treatment composition includes 0.1% to 5% by total weight of the one or more hydrophobic chemical compounds, the one or more chemical compounds that impart hydrophobic properties to the top layer, or combinations thereof by weight of the chemical treatment composition.

29. The reusable pad of claim 20 wherein the one or more plies of multifilament hydrophobic yarn for each of the first wicking sub-layer, the sub-layer of tuck yarns, and the second wicking sub-layer include one or more plies of multifilament polyester yarn.

30. The reusable pad of claim 20 wherein the first dpf value is in a range from about 1 to about 2 dpf, the second dpf value is in a range from about 2 to about 3 dpf, and the third dpf value is in a range from about 4 to about 5 dpf.

31. The reusable pad of claim 20 wherein the second wicking layer includes one or more plies of multifilament polyester yarn.

32. The reusable pad of claim 20 wherein the second wicking layer has a dpf value in a range from about 4 to about 5 dpf.

33. The reusable pad of claim 20 wherein the reusable pad defines a reusable incontinence pad.

34. The reusable pad of claim 20 wherein the reusable pad is used in or as a panty liner or a diaper.

35. The reuseable pad of claim 20 wherein the reusable pad can be washed, dried, and reused at least multiple times.

* * * * *

UNITED STATES PATENT AND TRADEMARK OFFICE
CERTIFICATE OF CORRECTION

PATENT NO. : 12,396,900 B2
APPLICATION NO. : 17/711483
DATED : August 26, 2025
INVENTOR(S) : Holbert, Jr. et al.

Page 1 of 1

It is certified that error appears in the above-identified patent and that said Letters Patent is hereby corrected as shown below:

In the Claims

Column 28, Lines 49-50, Claim 10, "smaller than the second dpf value with the second dpf value being smaller than the third dpf to provide the capillary" should be -- smaller than the second dpf value with the second dpf value being smaller than the third dpf value to provide the capillary --. Column 29, Lines 50-51, Claim 20, "second dpf value being smaller than the third dpf to provide a capillary gradient that promotes migration of" should be -- second dpf value being smaller than the third dpf value to provide a capillary gradient that promotes migration of --.

Signed and Sealed this
Fourth Day of November, 2025

John A. Squires
*Director of the United States Patent and Trademark Office*